United States Patent [19]
Platzek et al.

[11] Patent Number: 6,045,776
[45] Date of Patent: Apr. 4, 2000

[54] PROCESS FOR THE PRODUCTION OF METAL-COMPLEX CARBOXYLIC ACID AMIDES

[75] Inventors: Johannes Platzek; Bernd Raduchel; Heribert Schmitt-Willich; Klaus-Dieter Graske, all of Berlin, Germany

[73] Assignee: Schering Aktiengesellschaft, Germany

[21] Appl. No.: 08/982,381

[22] Filed: Dec. 2, 1997

Related U.S. Application Data

[60] Provisional application No. 60/032,851, Dec. 13, 1996.

[30] Foreign Application Priority Data

Dec. 4, 1996 [DE] Germany .................. 196 52 386

[51] Int. Cl.$^7$ .................................................. A61B 5/055
[52] U.S. Cl. .................. 424/9.365; 534/16; 540/465; 540/474; 556/50; 556/55; 556/63; 556/77; 556/105; 556/116; 556/134; 556/148; 514/836
[58] Field of Search .................. 424/9.365; 534/16; 540/465, 474; 564/138; 556/50, 55, 63, 77, 105, 116, 134, 148; 514/836; 600/420; 436/173, 806

[56] References Cited

U.S. PATENT DOCUMENTS

| | | | |
|---|---|---|---|
| 5,162,109 | 11/1992 | Rajagopalan et al. | 424/1.1 |
| 5,208,324 | 5/1993 | Klaveness et al. | 534/16 |
| 5,277,895 | 1/1994 | Platzek et al. | 424/9 |
| 5,364,613 | 11/1994 | Sieving et al. | 424/9 |
| 5,385,719 | 1/1995 | Unger et al. | 528/272 |
| 5,386,028 | 1/1995 | Tilstam et al. | 540/474 |
| 5,428,155 | 6/1995 | Sherry et al. | 540/474 |
| 5,508,388 | 4/1996 | deLearie et al. | 534/16 |
| 5,565,184 | 10/1996 | Dunn et al. | 424/1.65 |
| 5,804,163 | 9/1998 | Gibby et al. | 424/936.1 |

*Primary Examiner*—Gary E. Hollinden
*Attorney, Agent, or Firm*—Millen, White, Zelano & Branigan, P.C.

[57] ABSTRACT

The invention relates to a process for the production of metal-complex carboxylic acid amides, characterized in that a metal-complex carboxylic acid mixture that consists of the metal-complex carboxylic acid and at least one solubilizing substance in dimethyl sulfoxide (DMSO) is pretreated with a dehydrating reagent, optionally with the addition of a coupling adjuvant, and is then reacted with an amine of general formula I $$A(NH_2)_n \qquad (I),$$

in which

A stands for the radical of a natural or synthetic amine, and n stands for numbers 1 to 100.

31 Claims, No Drawings

PROCESS FOR THE PRODUCTION OF METAL-COMPLEX CARBOXYLIC ACID AMIDES

This application claims benefit to provisional application Ser. No. 60/032,851 filed Dec. 13, 1996.

BACKGROUND OF THE INVENTION

The invention relates to the object characterized in the claims, i.e., a new process for the production of metal-complex carboxylic acid amides.

Metal-complex carboxylic acid amides are used in a variety of ways in medical diagnosis and treatment. Such compounds and their use as contrast media, primarily in nuclear spin tomography (MRI), are described in, e.g., European Patent Applications No. 0255 471, 0331616, 0430863, 0481526, 0130934 and in International Patent Applications WO 96/02669 and WO 94/28940. Their production is carried out by coupling an amine with the activated carboxylic acid of a complexing agent, whose additional carboxylic acids generally must be present in protected form.

Anhydrides and N-hydroxysuccinimides are frequently used. After the existing acid protective groups are cleaved, the desired metal is introduced.

The following can be cited as the primary drawbacks of this method:

a) Incomplete coupling and associated separating problems of the reaction products. The unreacted amines generally have undesirable pharmacological properties.

b) Incomplete metal incorporation (complexing) into the complexing agent conjugates. An undesirable antidote action (impairing the cardiovascular system) as well as lower effectiveness of the product formed as a diagnostic agent (lower metal content of the contrast medium) are the result.

c) Protective group chemistry always results in additional reaction steps, in which the protective groups must be removed again. In this case, impairment of the pharmacological properties of the desired product can very easily occur. In addition, during the cleavage of the protective groups, large amounts of by-products accumulate that must then be disposed of. Therefore, avoidance of protective groups, especially for processes that are to be used on an industrial scale, is desirable.

d) The yield of the metal-complex carboxylic acid amides that are obtained according to the methods of the prior art is often unsatisfactory.

e) The incorporation of metal, mainly when macrocyclic complexing agents are used, must be performed at high temperatures. This also leads to impairment of the purity of the reaction product.

SUMMARY OF THE INVENTION

The object of the invention thus is to make available a process for the production of metal-complex carboxylic acid amides that avoids the above-mentioned drawbacks or at least mitigates them.

It has been found that, surprisingly enough, this object is achieved by this invention, i.e., by the process for the production of metal-complex carboxylic acid amides, characterized in that a metal-complex carboxylic acid mixture that consists of the metal-complex carboxylic acid and at least one solubilizing substance in dimethyl sulfoxide (DMSO) is pretreated with a dehydrating reagent, optionally with the addition of a coupling adjuvant, and is then reacted with an amine of general formula I $$A(NH_2)_n \qquad (I),$$

in which

A stands for the radical of a natural or synthetic amine, and n stands for numbers 1 to 100.

The mixture of metal-complex carboxylic acid and at least one solubilizing substance used in the coupling reaction in an amount of up to 5, preferably 0.5–2 molar equivalents relative to the metal-complex carboxylic acid, can be produced both in an upstream reaction stage and isolated (e.g., by concentration by evaporation, freeze-drying or spray drying of an aqueous or water-miscible solution of the components, or by precipitation from such a solution with an organic solvent), and then reacted in DMSO with dehydrating reagent and optionally a coupling adjuvant, as well as formed in situ by the addition of solubilizing substance(s) to the DMSO suspension of metal-complex carboxylic acid, dehydrating reagent, and optionally a coupling adjuvant.

The reaction solution that is produced according to one of these processes is kept for 1 to 24, preferably 3 to 12 hours at temperatures of 0 to 50° C., preferably at room temperature for pretreatment (acid activation). Then, an amine of general formula I is added without solvent or is dissolved, preferably in DMSO, in water or in solvents that are mixed with water. For amide coupling, the reaction solution thus obtained is kept at temperatures of 0 to 70° C., preferably 30 to 60° C., for 1 to 48, preferably 8 to 24 hours.

In some cases, it has proven advantageous to use the amine in the form of its salts, e.g., as hydrobromide or hydrochloride, in the reaction. To release the amine, a base such as, e.g., triethylamine, diisopropylethylamine, N-methylmorpholine, pyridine, tripropylamine, tributylamine, lithium hydroxide, lithium carbonate, sodium hydroxide or sodium carbonate is added.

The isolation of the reaction product is carried out according to the methods known to one skilled in the art, preferably by precipitation with organic solvents, preferably acetone, 2-butanone, diethyl ether, ethyl acetate, methyl-t-butyl ether, isopropanol or their mixtures. Subsequent purification can be carried out by, for example, chromatography, crystallization, or ultrafiltration.

As solubilizing substances, alkali, alkaline-earth, trialkylammonium and tetraalkylammonium salts; ureas, N-hydroxyimides, hydroxyaryltriazoles, substituted phenol, and salts of heterocyclic amines are suitable. By way of example there can be mentioned: lithium chloride, lithium bromide, lithium iodide, sodium bromide, sodium iodide, lithium methanesulfonate, sodium methanesulfonate, lithium-p-toluenesulfonate, sodium-p-toluenesulfonate, potassium bromide, potassium iodide, sodium chloride, magnesium bromide, magnesium chloride, magnesium iodide, tetraethylammonium-p-toluenesulfonate, tetramethylammonium-p-toluenesulfonate, pyridinium-p-toluenesulfonate, triethylammonium-p-toluenesulfonate, 2-morpholinoethylsulfonic acid, 4-nitrophenol, 3,5-dinitrophenol, 2,4-dichlorophenol, N-hydroxysuccinimide, N-hydroxyphthalimide, urea, tetramethylurea, N-methylpyrrolidone, formamide as well as cyclic ureas, whereby the five first-mentioned are preferred.

As dehydrating reagents, all agents that are known to one skilled in the art are used (see, e.g., Houben-Weyl, Methoden der Organischen Chemie [Methods of Organic Chemistry], Vol. XV/2, Georg Thieme-Verlag, Stuttgart, 1974 and J. Chem. Research (S) 1996, 302).

By way of example, carbodiimides and onium reagents, such as, e.g., dicyclohexylcarbodiimide (DCCI), 1-ethyl-3-(3-dimethylaminopropyl)-carbodiimide-hydroxychloride (EDC), benzotriazol-1-yloxytris(dimethylamino)-phosphoniumhexafluorophosphate (BOP) and O-(benzotriazol-1-yl)-1,1,3,3-tetramethyluroniumhexafluorophosphate (HBTU), preferably DCCI, can be mentioned.

As coupling adjuvants that are optionally to be used, all that are known to one skilled in the art are suitable (Houben-Weyl, Methoden der organischen Chemie, Vol. XV/2, Georg Thieme-Verlag, Stuttgart, 1974). By way of example, 4-nitrophenol, N-hydroxysuccinimide, 1-hydroxybenzotriazole, 1-hydroxy-7-azabenzotriazole, 3,5-dinitrophenol and pentafluorophenol can be mentioned. Preferred are 4-nitrophenol and N-hydroxysuccinimide, and especially preferred in this case is the first-mentioned reagent.

As amines of general formula I, monoamines (n=1) and polyamines (n=2–100) are suitable. Of the polyamines, those with n=2 to 50 are preferred, and especially preferred are those with n=12 to 36. By way of example, dendrimers (as mentioned in, e.g., Polymer Journal 17, 117 (1985), U.S. Pat. No. 4,587,329, EP 0430863, WO 96/01655), proteins, polylysines (as mentioned in, e.g., EP 0481526 and EP 0331616), aminopolysaccharides (as mentioned in, e.g., WO 94/28940), polyvinylamines, polyalkylamines, poly[N(2-aminoethyl)]methacrylamides, polynucleotides (see, e.g., WO 96/02669), antisense-polynucleotides, polypeptides, antibiotics, nucleosides, aminoterpenes, aminoporphyrins (see, e.g., WO 94/07894), amino steroids and amino sugars can be mentioned. Preferred are dendrimers, mainly those that do not contain any amino groups that can be protonated in radical A of general formula I. Especially preferred are the cascade polymeramines mentioned in WO 96/01655, quite especially preferred is the 24-mer polyamine based on N,N,N',N',N'',N''-hexakis[2-(trilysyl-amino)-ethyl]trimesic acid triamide (see Example 12).

As metal-complex carboxylic acids, linear compounds (e.g., the compounds mentioned in DE 19507822 and EP 0450742) and macrocyclic compounds (e.g., the compounds mentioned in EP 0485045) are suitable. Preferred are macrocycles based on the 1,4,7,10-tetraazacyclododecane skeleton. Especially preferred are those of general formula II

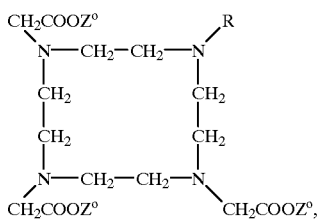

(II)

whereby $Z^0$ stands for a metal ion equivalent of atomic numbers 25, 26, 39, 57–71, 83 and R stands for a CHX$^1$—CO—NH—CHY$^1$—(CH$_2$)$_f$—COOH group, in which X$^1$ and Y$^1$, independently of one another, mean a hydrogen atom, a straight-chain or branched C$_1$–C$_7$ alkyl radical, a phenyl or benzyl group, and f means numbers 0 to 9.

For radical X$^1$ or Y$^1$, methyl, ethyl, propyl, butyl or hydrogen, methyl, isopropyl, phenyl and benzyl can be mentioned by way of example. Methyl or hydrogen is preferred.

Index f preferably stands for numbers 0, 1 or 2.

Of the above-mentioned lanthanides, gadolinium and dysprosium are preferred. As complexing agents of general formula II ($Z^0$=hydrogen), 10-[4-carboxy-1-methyl-2-oxo-3-azabutyl]-1,4,7,10-tetraazacyclododecane-1,4,7-triacetic acid is especially preferred.

The synthesis of these compounds is carried out in that compounds of general formula III

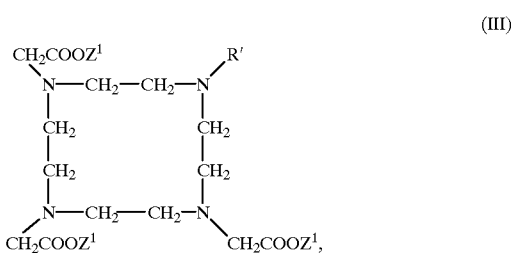

(III)

in which

R' has the meaning of R, whereby the carboxyl group contained therein is optionally present in protected form and $Z^1$ stands for a hydrogen atom or a carboxyl protective group, after cleavage of the optionally present carboxyl protective groups, are reacted in a way known in the art with a metal oxide or metal salt of an element of atomic numbers 25, 26, 39, 57–71 and 83.

The introduction of the desired metal ions is carried out in the way in which it was disclosed in, e.g., Patents EP 71564, EP 130934 and DE-3401052, by the metal oxide or a metal salt (for example, the nitrate, acetate, carbonate, chloride or sulfate) of the element of the desired atomic numbers being dissolved or suspended in water and/or a lower alcohol (such as methanol, ethanol or isopropanol) and being reacted with a solution or suspension of the equivalent amount of complexing agent of general formula III.

If $Z^1$ stands for an acid protective group, e.g., straight-chain or branched C$_1$–C$_6$ alkyl, aryl and aralkyl groups, for example, the methyl, ethyl, propyl, butyl, phenyl, benzyl, diphenylmethyl, triphenylmethyl, bis(p-nitrophenyl)-methyl groups, as well as trialkylsilyl groups, are suitable. The t-butyl group is preferred.

The cleavage of the protective groups is carried out according to the processes known to one skilled in the art, by, for example, hydrolysis, hydrogenolysis, alkaline saponification of esters with alkali in aqueous-alcoholic solution at temperatures of 0° C. to 50° C., acid saponification with mineral acids or in the case of, e.g., tert-butyl esters with the aid of trifluoroacetic acid. [Protective Groups in Organic Synthesis, 2nd Edition, T. W. Greene and P. G. M. Wuts, John Wiley and Sons, Inc., New York, 1991].

Compounds of general formula III can be obtained by reaction of α-halocarboxylic acid esters or α-haloacids of general formula IV

(IV), in which
Z$^1$ has the above-mentioned meaning and Hal stands for chlorine, bromine or iodine,
with compounds of general formula V

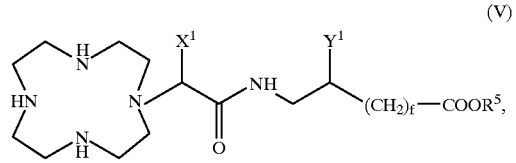

(V)

in which
R$^5$ stands for a hydrogen atom, or an acid protective group and
X$^1$, Y$^1$ and f have the above-mentioned meaning.

If Z$^1$ and R$^5$ in each case stand for an acid protective group, the latter can have varying meanings, so that Z$^1$ (e.g., benzyl) can be cleaved optionally selectively (e.g., by hydrogenolysis) in the presence of R$^5$ protective groups (e.g., t-butyl).

If Z$^1$ stands for an acid protective group, the reaction is carried out preferably in solvents such as methylene chloride, dimethylformamide, acetonitrile, tetrahydrofuran, dioxane, chloroform, lower alcohols such as methanol, ethanol and isopropanol, as well as mixtures of the above-mentioned solvents with water.

When a haloacid is used as an educt, water is the preferred working medium.

As acid traps, organic bases such as pyridine, triethylamine or diisopropylethylamine or inorganic bases such as sodium hydroxide, lithium hydroxide, potassium hydroxide, calcium hydroxide or sodium carbonate, potassium carbonate, sodium bicarbonate or lithium carbonate are used. Alkylation is performed at temperatures of between 0–100° C., but preferably at 20–80° C.

Compounds of general formula V are obtained by reaction of cyclene (formula VI)

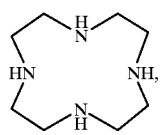

(VI)

with compounds of general formula VII

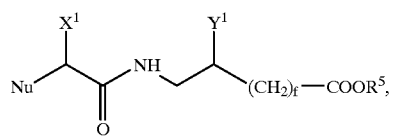

(VII)

in which
X$^1$, Y$^1$, R$^5$ and f have the above-mentioned meaning and Nu stands for a nucleofuge. As nucleofuges, chloride, bromide, iodide, mesylate, tosylate or triflate can be mentioned.

The reaction is carried out in solvents, such as chloroform, methylene chloride, tetrahydrofuran, dioxane, dimethylformamide, dimethyl sulfoxide or else in water at temperatures of 0° C. to 100° C., but preferably at 20°–60°.

If desired, an organic or inorganic base can be added. Triethylamine, pyridine, sodium carbonate, sodium hydroxide or potassium hydroxide can be mentioned by way of example.

Compounds of general formula VII are obtained by reaction of compounds of general formula VIII

(VIII)

in which
Nu and X$^1$ have the above-mentioned meaning, with compounds of general formula IX

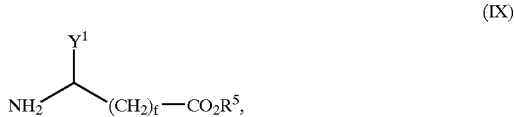

(IX)

in which
Y$^1$, f and R$^5$ have the above-indicated meaning.

The reaction is carried out according to peptide-chemistry methods that are known to one skilled in the art. Thus, for example, a derivative, such as, e.g., an acid chloride, acid bromide or active ester (such as, e.g., NHS-ester), can be produced, for example, from the acid of general formula VIII, whereby said derivative is condensed with an amino acid (optionally terminally-protected).

Compounds of general formula VIII, as well as their acid chlorides and acid bromides are commercially available. Compounds of general formula IX are also commercially available as free amino acids or in protected form.

As an alternative, compounds of general formula III can be obtained by reaction of compounds of general formula X

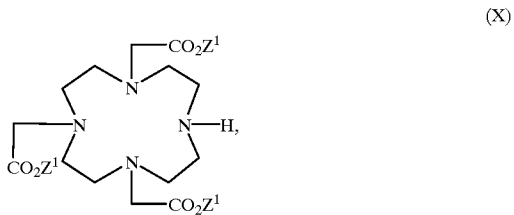

(X)

in which Z$^1$ has the above-mentioned meaning (see, e.g., EP 0255471), with compounds of general formula VII, after cleavage of the optionally present acid protective groups.

The reaction is carried out in solvents, such as, for example, acetonitrile, dimethylformamide, tetrahydrofuran, dioxane or lower alcohols such as methanol, ethanol or i-propanol as well as mixtures of the latter with water; but the reaction can also be performed in pure water. The work is generally done at temperatures of 20° C.–100° C..

As acid traps, organic or inorganic bases are used. Triethylamine, pyridine, 4-dimethylaminopyridine, sodium hydroxide, potassium hydroxide, potassium carbonate and sodium carbonate can be mentioned by way of example. Metal hydrides such as sodium hydride and calcium hydride can also be used, but only in the case of aprotic solvents.

The addition of a catalytic amount of an iodide has proven advantageous. Sodium iodide, potassium iodide, lithium iodide or tetrabutylammonium iodide can be mentioned by way of example.

The purification of the metal complexes of general formula II is carried out by, for example, chromatography on silica gel or RP-18.

Most of the metal complexes of general formula II can be crystallized from alcohols such as methanol, ethanol or isopropanol or else from their mixtures with water.

It has also proven advantageous to dissolve the metal complexes in alcohols or mixtures of alcohols with water and to precipitate them by adding acetone in drops.

The drying of metal-complex carboxylic acids takes place advantageously in a vacuum at temperatures of 20°–200° C., preferably 50°–130° C., within about 6 hours to 3 days.

The metal-complex carboxylic acids of general formula II that are thus obtained are stored in a moisture-free environment and can be introduced directly into a coupling reaction.

The process according to the invention is distinguished by virtually complete coupling of amines with the metal-complex carboxylic acids, such that no problems with respect to the separation of unreacted or partially reacted educts occur. The amide conjugates that are thus formed also contain virtually no metal-free complexing agent units. Both result in physiologically more compatible compounds than the conjugates that can be produced according to the prior art.

Since no protective groups need to be introduced or cleaved in the process according to the invention, and the incorporation of metal, which stresses the molecule (high temperature, low pH), is avoided in the last reaction step, the products are obtained in high purity. In addition, the yield of the process according to the invention is surprisingly high.

Another advantage of the process according to the invention lies in the fact that the process is also suitable for reactions on an industrial scale, since the reaction can be performed in highly-concentrated solution.

Examples 1 to 11 below are used to explain the synthesis of metal-complex carboxylic acids of general formula II:

EXAMPLE 1 a) N-(2-Bromopropionyl)glycine-benzyl Ester 55.9 g (326.1 mmol) of 2-bromopropionic acid chloride is added in drops at 0° C. to 100 g (296.4 mmol) of glycine benzyl ester-p-toluenesulfonic acid salt and 33.0 g (326.1 mmol) of triethylamine in 400 ml of methylene chloride. The temperature is not allowed to exceed 5° C. After the addition is completed, it is stirred for one hour at 0° C., then for 2 hours at room temperature. 500 ml of ice water is added, and the water phase is set at pH 2 with 10% aqueous hydrochloric acid. The organic phase is separated, washed once each with 300 ml of 5% aqueous soda solution and 400 ml of water. The organic phase is dried on magnesium sulfate and evaporated to dryness in a vacuum. The residue is recrystallized from diisopropyl ether.

Yield: 68.51 g (75% of theory) of a colorless, crystalline powder

Melting point: 69–70° C.

Elementary analysis: Cld: C 48.02 H 4.70 N 4.67 Br 26.62 Fnd: C 47.91 H 4.82 N 4.51 Br 26.47 b) 1-[4-(Benzyloxycarbonyl)-1-methyl-2-oxo-3-azabutyl]-1,4,7,10-tetraazacyclododecane 50 g (162.2 mmol) of the title compound of Example 1a) is added to 55.8 g (324.4 mmol) of 1,4,7,10-tetraazacyclododecane, dissolved in 600 ml of chloroform, and it is stirred overnight at room temperature. 500 ml of water is added, the organic phase is separated and in each case washed twice with 400 ml of water. The organic phase is dried on magnesium sulfate and evaporated to dryness in a vacuum. The residue is chromatographed on silica gel (mobile solvent: chloroform/methanol/aqueous 25% ammonia=10:5:1).

Yield: 40.0 g [63% of theory relative to the 1a) used] of a slightly yellowish viscous oil.

Elementary analysis: Cld: C 61.36 H 8.50 N 17.89 Fnd: C 61.54 H 8.68 N 17.68 c) 10-[4-(Benzyloxycarbonyl)-1-methyl-2-oxo-3-azabutyl]-1,4,7-tris(tert-butoxycarbonylmethyl)-1,4,7,10-tetraazacyclododecane (Sodium Bromide Complex)

33 g (169 mmol) of bromoacetic acid-tert-butyl ester is added to 20 g (51.08 mmol) of the title compound of Example 1b) and 17.91 (169 mmol) of sodium carbonate in 300 ml of acetonitrile, and it is stirred for 24 hours at 60° C. It is cooled to 0° C., the salts are filtered out, and the filtrate is evaporated to dryness. The residue is chromatographed on silica gel (mobile solvent: ethyl acetate/ethanol: 15:1). The fractions that contain the product are concentrated by evaporation, and the residue is recrystallized from diisopropyl ether.

Yield: 34.62 g (81% of theory) of a colorless, crystalline powder

Melting point: 116–117° C.

Elementary analysis: Cld: C 54.54 H 7.59 N 8.37 Na 2.74 Br 9.56 Fnd: C 54.70 H 7.65 N 8.24 Na 2.60 Br 9.37 d) 10-(4-Carboxy-1-methyl-2-oxo-3-azabutyl)-1,4,7-tris(tert-butoxycarbonylmethyl)-1,4,7,10-tetraazacyclododecane (Sodium Bromide Complex)

30 g (35.85 mmol) of the title compound of Example 1c) is dissolved in 500 ml of isopropanol, and 3 g of palladium catalyst (10% Pd/C) is added. It is hydrogenated overnight at room temperature. Catalyst is filtered out, the filtrate is evaporated to dryness in a vacuum and recrystallized from acetone.

Yield: 22.75 g (85% of theory) of a colorless, crystalline powder

Melting point: 225° C. (decomposition)

Elementary analysis: Cld: C 49.86 H 7.69 N 9.38 Na 3.07 Br 10.71 Fnd: C 49.75 H 7.81 N 9.25 Na 2.94 Br 10.58 e) 10-[4-Carboxy-1-methyl-2-oxo-3-azabutyl]-1,4,7,10-tetraazacyclododecane-1,4,7-triacetic Acid 77 g (103.1 mmol) of the title compound of Example 1d is dissolved in 500 ml of trifluoroacetic acid and stirred for 3 hours at room temperature. It is evaporated to dryness, the residue is taken up in 300 ml of water, and the solution is added to a column, filled with Reillex® 425 PVP. It is eluted with water. The product-containing fractions are combined and evaporated to dryness, and the residue is recrystallized from methanol/acetone.

Yield: 44.04 g (84% of theory) of a colorless, hygroscopic solid

Water content: 6.5%

Elementary analysis (relative to anhydrous substance): Cld: C 47.99 H 6.99 N 14.73 Fnd: C 47.83 H 7.12 N 14.55 f) Gadolinium Complex of 10-[4-carboxy-1-methyl-2-oxo-3-azabutyl]-1,4,7,10-tetraazacyclododecane-1,4,7-triacetic Acid 15.27 g (42.06 mmol) of gadolinium oxide is added to 40 g (84.12 mmol) of the title compound of Example 1e, dissolved in 400 ml of water, and it is heated for 3 hours to 90° C. It is evaporated to dryness (vacuum), and the residue is recrystallized from 90% aqueous ethanol. The crystals are suctioned off, washed once with ethanol, then with acetone and finally with diethyl ether and dried in a vacuum furnace at 130° C. (24 hours).

Yield: 50.53 g (93% of theory) of a colorless, crystalline powder

Water content: 2.5%

Elementary analysis (relative to anhydrous substance): Cld: C 36.24 H 4.80 N 11.12 Gd 24.97 Fnd: C 36.35 H 4.95 N 10.98 Gd 24.80

EXAMPLE 2

Dysprosium Complex of 10-[4-carboxy-1-methyl-2-oxo-3-azabutyl]-1,4,7,10-tetraazacyclododecane-1,4,7-triacetic Acid 7.84 g (21.03 mmol) of dysprosium oxide is added to 20 g (42.06 mmol) of the title compound of Example 1e, dissolved in 200 ml of water, and it is heated for 3 hours to 90° C. It is evaporated to dryness (vacuum), and the residue is recrystallized from 90% aqueous ethanol. The crystals are suctioned off, washed once with ethanol, then with acetone and finally with diethyl ether and dried in a vacuum furnace at 130° C. (24 hours).

Yield: 24.98 (91% of theory) of a colorless, crystalline powder

Water content: 2.7%

Elementary analysis (relative to anhydrous substance):
Cld: C 35.94 H 4.76 N 11.03 Dy 25.59 Fnd: C 35.85 H 4.91 N 10.90 Dy 25.42

EXAMPLE 3

Ytterbium Complex of 10-[4-carboxy-1-methyl-2-oxo-3-azabutyl]-1,4,7,10-tetraazacyclododecane-1,4,7-triacetic Acid 8.29 g (21.03 mmol) of ytterbium oxide is added to 20 g (42.06 mmol) of the title compound of Example 1e, dissolved in 200 ml of water, and it is heated for 3 days to 90° C. It is evaporated to dryness (vacuum), and the residue is recrystallized from 90% aqueous ethanol. The crystals are suctioned off, washed once with ethanol, then with acetone and finally with diethyl ether and dried in a vacuum furnace at 130° C. (24 hours).

Yield: 21.79 (78% of theory) of a colorless, crystalline powder

Water content: 2.8%

Elementary analysis (relative to anhydrous substance):
Cld: C 35.35 H 4.68 N 10.85 Yb 26.81 Fnd: C 35.25 H 4.79 N 10.68 Yb 26.61

EXAMPLE 4 a) N-(2-Bromobutyryl)-glycine Benzyl Ester 65.96 g (355.7 mmol) of α-bromobutyric acid chloride is added in drops at 0° C. to 100 g (296.4 mmol) of glycine benzyl ester p-toluenesulfonic acid salt and 89.98 g (889.2 mmol) of triethylamine in 500 ml of methylene chloride. In this case, the temperature remains between 0° C.–5° C. 1000 ml of 5% aqueous hydrochloric acid is added, and the organic phase is separated.

The organic phase is extracted once more with 500 ml of 5% aqueous hydrochloric acid, dried on magnesium sulfate and evaporated to dryness in a vacuum. The residue is recrystallized from diisopropyl ether.

Yield: 75.43 g (81% of theory) of a colorless, crystalline powder

Elementary analysis: Cld: C 49.70 H 5.13 N 4.46 Br 25.43 Fnd: C 49.51 H 5.27 N 4.31 Br 25.28 b) 10-[4-(Benzyloxycarbonyl)-1-ethyl-2-oxo-3-azabutyl]-1,4,7,10-tetraazacyclododecane-1,4,7-triacetic Acid-tri-tert-butyl Ester 500 ml of acetonitrile is added to 50 g (159.14 mmol) of the title compound of Example 4a, 36.98 g (79.6 mmol) of 1,4,7-tris(tert-butoxy-carbonylmethyl)-1,4,7,10-tetraazacyclododecane (=D03A-tri-tert-butyl ester), 44 g (318.4 mmol) of potassium carbonate and 1 g (60 mmol) of potassium iodide, and it is refluxed for 12 hours. The salts are filtered out, and the filtrate is evaporated to dryness in a vacuum. The residue is dissolved in 800 ml of dichloromethane and extracted twice with 300 ml of 5% aqueous sodium carbonate solution each. The organic phase is dried on magnesium sulfate and concentrated by evaporation. After chromatography on silica gel (mobile solvent: dichloromethane/methanol=20:1), 19.11 g of the title compound (32.1% of theory) is obtained as a colorless foam.

Elementary analysis: Cld: C 62.63 H 8.76 N 9.36 Fnd: C 62.51 H 8.91 N 9.18 c) 10-(4-Carboxy-1-ethyl-2-oxo-3-azabutyl)-1,4,7,10-tetraazacyclododecane-1,4,7-triacetic Acid-tri-tert-butyl Ester 19 g (25.40 mmol) of the title compound of Example 4b is dissolved in 300 ml of isopropanol, and 2 g of palladium catalyst (10% Pd/C) is added. It is hydrogenated overnight at room temperature. Catalyst is filtered out, and the filtrate is evaporated to dryness.

Yield: 16.54 g (99% of theory) of a viscous oil

Elementary analysis: Cld: C 58.43 H 9.04 N 10.65 Fnd: C 58.65 H 9.27 N 10.47 d) 10-(4-Carboxy-1-ethyl-2-oxo-3-azabutyl)-1,4,7,10-tetraazacyclododecane-1,4,7-triacetic Acid 16 g (24.32 mmol) of the title compound of Example 4c is dissolved in 100 ml of trifluoroacetic acid, and it is stirred for 3 hours at room temperature. It is evaporated to dryness, the residue is taken up in 50 ml of water, and the solution is added to a column, filled with Reillex® 425 PVP. It is eluted with water. The product-containing fractions are combined and evaporated to dryness, and the residue is recrystallized from methanol/acetone.

Yield: 10.10 g (79% of theory) of a colorless, hygroscopic solid

Water content: 6.9%

Elementary analysis (relative to anhydrous substance):
Cld: C 49.07 H 7.21 N 14.31 Fnd: C 49.28 H 7.39 N 14.15 e) Gadolinium Complex of 10-(4-carboxy-1-ethyl-2-oxo-3-azabutyl)-1,4,7,10-tetraazacyclododecane-1,4,7-triacetic Acid 3.33 g (9.19 mmol) of gadolinium oxide is added to 9 g (18.38 mmol) of the title compound of Example 4d, dissolved in 70 ml of water, and it is heated for 3 hours to 90° C. It is evaporated to dryness (vacuum), and the residue is recrystallized from 90% aqueous ethanol. The crystals are suctioned off, washed once with ethanol, then with acetone and finally with diethyl ether and dried in a vacuum furnace at 130° C. (24 hours).

Yield: 11.44 g (94% of theory) of a colorless, crystalline powder

Water content: 2.8%

Elementary analysis (relative to anhydrous substance):
Cld: C 37.32 H 5.01 N 10.88 Gd 24.43 Fnd: C 37.15 H 5.21 N 10.65 Gd 24.25

EXAMPLE 5

Dysprosium Complex of 10-(4-carboxy-1-ethyl-2-oxo-3-azabutyl)-1,4,7,10-tetraazacyclododecane-1,4,7-triacetic Acid 3.81 g (10.21 mmol) of dysprosium oxide is added to 10 g (20.43 mmol) of the title compound of Example 4d, dissolved in 80 ml of water, and it is heated for 3 hours to 90° C. It is evaporated to dryness (vacuum), and the residue is recrystallized from 90% aqueous ethanol. The crystals are suctioned off, washed once with ethanol, then with acetone and finally with diethyl ether and dried in a vacuum furnace at 130° C. (24 hours).

Yield: 12.40 g (91% of theory) of a colorless, crystalline powder

Water content: 2.7%

Elementary analysis (relative to anhydrous substance):
Cld: C 37.01 H 4.97 N 10.79 Dy 25.04 Fnd: C 36.85 H 5.13 N 10.61 Dy 24.87

EXAMPLE 6 a) N-[2-Bromo-2-phenyl-acetyl]-glycolic Acid-tert-butyl Ester 72.69 g (311.3 mmol) of a-bromophenylacetic acid chloride is added in drops at 0° C. to 50 g (296.5 mmol) of glycine-tert-butyl ester hydrochloride salt and 90 g (889.5 mmol) of triethylamine in 500 ml of methylene chloride. In this case, the temperature remains between 0° C.–5° C. 1000 ml of 5% aqueous hydrochloric acid is added, and the organic phase is separated. The organic phase is extracted once more with 500 ml of 5% aqueous hydrochloric acid, dried on magnesium sulfate and evaporated to dryness in a vacuum. The residue is recrystallized from diisopropyl ether/n-hexane.

Yield: 78.8 g (81% of theory)

Elementary analysis: Cld: C 51.23 H 5.53 N 4.27 Br 24.35 Fnd: C 51.15 H 5.66 N 4.11 Br 24.18 b) 1-[4-(tert-Butoxycarbonyl)-oxo-1-phenyl-3-azabutyl]-4,7,10-tris(tert-butoxycarbonylmethyl)-1,4,7,10-tetraazacyclododecane 500 ml of acetonitrile is added to 50 g (159.14 mmol) of the title compound of Example 6a, 53.12 g (114.3 mmol) of 1,4,7-tris(tert-butoxy-carboxymethyl)-1,4,7,10-tetraazacyclododecane (=D03A-tri-tert-butyl ester), 63.16 g (457.0 mmol) of potassium carbonate and 1 g (6 mmol) of potassium iodide, and it is refluxed for 12 hours. The salts are filtered out, and the filtrate is evaporated to dryness in a vacuum. The residue is dissolved in 1000 ml of dichloromethane, and it is extracted twice with 400 ml of 5% aqueous sodium carbonate solution each. The combined organic phases are dried on magnesium sulfate and concentrated by evaporation. After chromatography on silica gel (mobile solvent: dichloromethane/methanol=20:1), 27 g of the title compound (31% of theory) is obtained as a colorless foam.

Elementary analysis: Cld: C 63.05 H 8.86 N 9.19 Fnd: C 62.91 H 8.98 N 9.02 c) 1-(4-Carboxy-2-oxo-1-phenyl-3-azabutyl)-4,7,10-tris(carboxymethyl)-1,4,7,10-tetraazacyclododecane 26 g (34.12 mmol) of the title compound of Example 6b is dissolved in 300 ml of trifluoroacetic acid, and it is stirred for 3 hours at room temperature. It is evaporated to dryness, the residue is taken up in 80 ml of water, and the solution is added to a column, filled with Reillex® 425 PVP. It is eluted with water. The product-containing fractions are combined and evaporated to dryness, and the residue is recrystallized from methanol/acetone.

Yield: 16.22 g (81% of theory) of a colorless, hygroscopic solid

Water content: 8.4%

Elementary analysis (relative to anhydrous substance):
Cld: C 53.62 H 6.56 N 13.03 Fnd: C 53.48 H 6.71 N 12.87 d) Gadolinium Complex of 1-(4-carboxy-2-oxo-1-phenyl-3-azabutyl)-4,7,10-tris(carboxymethyl)-1,4,7,10-tetraazacyclododecane 5.06 g (13.95 mmol) of gadolinium oxide is added to 15 g (27.90 mmol) of the title compound of Example 6c, dissolved in 200 ml of water, and it is heated for 3 hours to 90° C. It is evaporated to dryness (vacuum), and the residue is recrystallized from 90% aqueous ethanol. The crystals are suctioned off, washed once with ethanol, then with acetone and finally with diethyl ether and dried in a vacuum furnace at 130° C. (24 hours).

Yield: 18.27 g (92% of theory) of a colorless, crystalline powder

Water content: 2.8%

Elementary analysis (relative to anhydrous substance):
Cld: C 41.67 H 4.66 N 10.12 Gd 22.73 Fnd: C 41.40 H 4.80 N 9.95 Gd 22.51

EXAMPLE 7 a) N-(2-Bromopropionyl)-β-alanine 72.69 g (311.3 mmol) of α-bromopropionic acid chloride is added in drops at 0° C. to 40 g (448.98 mmol) of β-alanine and 90 g (889.5 mmol) of triethylamine in 500 ml of methylene chloride. In this case, the temperature remains between 0° C.–5° C. 1000 ml of 5% aqueous hydrochloric acid is added, and the organic phase is separated. The organic phase is extracted once more with 500 ml of 5% aqueous hydrochloric acid, dried on magnesium sulfate and evaporated to dryness in a vacuum. The residue is recrystallized from acetone/diisopropyl ether.

Yield: 62.37 g (62% of theory)

Elementary analysis: Cld: C 32.16 H 4.50 N 6.25 Br 35.66 Fnd: C 32.02 H 4.65 N 6.13 Br 35.74 b) 10-(5-Carboxy-1-methyl-2-oxo-3-azapentyl)-1,4,7,10-tetraazacyclododecane-1,4,7-triacetic Acid 46.38 g (133.9 mmol) of 1,4,7-tris(carboxymethyl)-1,4,7,10-tetraazacyclododecane (=D03A), 129.54 g (937.3 mmol) of potassium carbonate and 1 g (6 mmol) of potassium iodide are added to 60 g (267.80 mmol) of the title compound of Example 7a, dissolved in 300 ml of acetonitrile/200 ml of water. It is refluxed for 12 hours. It is evaporated to dryness in a vacuum, the residue is taken up in 500 ml of methanol, and then the salts are filtered out. The filtrate is evaporated to dryness, the residue is taken up in 300 ml of water and set at pH 1 with 5N hydrochloric acid. Then purification is done on a column filled with Reillex® 425 PVP. It is eluted with water. The product-containing fractions are evaporated to dryness in a vacuum, and the residue is recrystallized from methanol/acetone.

Yield: 19.19 g (27% of theory) of a colorless solid

Water content: 7.8%

Elementary analysis (relative to anhydrous substance):
Cld: C 49.07 H 7.21 N 14.31 Fnd: C 48.85 H 7.31 N 14.19 c) Gadolinium Complex of 10-(5-carboxy-1-methyl-2-oxo-3-azapentyl)-1,4,7,10-tetraazacyclododecane-1,4,7-triacetic Acid 6.66 g (18.38 mmol) of gadolinium oxide is added to 18 g (36.77 mmol) of the title compound of Example 7b, dissolved in 300 ml of water, and it is heated for 3 hours to 90° C. It is evaporated to dryness (vacuum), and the residue is recrystallized from 90% aqueous ethanol. The crystals are suctioned off, washed once with ethanol, then with acetone and finally with diethyl ether and dried in a vacuum furnace at 130° C. (24 hours).

Yield: 21.6 g (89% of theory) of a colorless, crystalline powder

Water content: 2.5%

Elementary analysis (relative to anhydrous substance):
Cld: C 37.32 H 5.01 N 10.88 Gd 24.43 Fnd: C 37.15 H 5.21 N 10.67 Gd 24.25

EXAMPLE 8 a) N-(2-Bromopropionyl)-11-aminoundecanoic Acid 30.65 g (178.8 mmol) of α-bromopropionic acid chloride is added in drops at 0° C. to 30 g (149 mmol) of 11-aminoundecanoic acid and 45.24 g (447.1 mmol) of triethylamine in 600 ml of methylene chloride. In this case, the temperature remains between 0° C.–5° C. 800 ml of 5% aqueous hydrochloric acid is added, and the organic phase is separated. The organic phase is extracted once more with 300 ml of 5% aqueous hydrochloric acid, dried on magnesium sulfate and evaporated to dryness in a vacuum. The residue is recrystallized from acetone/diisopropyl ether.

Yield: 25.55 g (51% of theory)

Elementary analysis: Cld: C 50.01 H 7.79 N 4.17 Br 23.76 Fnd: C 49.82 H 7.95 N 4.03 Br 23.59 b) 10-(13-Carboxy-1-methyl-2-oxo-3-aza-tridecyl)-1,4,7,10-tetraazacyclododecane-1,4,7-triacetic Acid 12.88 g (37.18 nmol) of 1,4,7-triscarboxymethyl-1,4,7,10-tetraazacyclododecane (=D03A), 35.97 g (260.3 mmol) of potassium carbonate and 1 g (6 mmol) of potassium iodide are added to 25 g (74.35 mmol) of the title compound of Example 8a, dissolved in 250 ml of acetonitrile/150 ml of water. It is refluxed for 12 hours. It is evaporated to dryness in a vacuum, the residue is taken up in 300 ml of methanol, and then the salts are filtered out. The filtrate is evaporated to dryness, the residue is taken up in 300 ml of water, and it is set at pH 1 with 5N hydrochloric acid. Then purification is done on a column filled with Reillex® 425 PVP. It is eluted with water. The product-containing fractions are evaporated to dryness in a vacuum, and the residue is recrystallized from methanol/acetone.

Yield: 6.63 g (27% of theory) of a colorless solid

Water content: 8.9%

Elementary analysis (relative to anhydrous substance): Cld: C 55.89 H 8.54 N 11.64 Fnd: C 55.71 H 8.70 N 11.57 c) Gadolinium Complex of 10-(13-carboxy-1-methyl-2-oxo-3-azatridecyl)-1,4,7,10-tetraazacyclododecane-1,4,7-triacetic Acid 1.81 g (4.98 mmol) of gadolinium oxide is added to 6 g (9.97 mmol) of the title compound of Example 8b, dissolved in 80 ml of water, and it is heated for 3 hours to 90° C. It is evaporated to dryness (vacuum), and the residue is recrystallized from 90% aqueous 2-propanol. The crystals are suctioned off, washed once with ethanol, then with acetone and finally with diethyl ether and dried in a vacuum furnace at 130° C. (24 hours).

Yield: 6.75 g (87% of theory) of a colorless, crystalline powder

Water content: 2.9%

Elementary analysis (relative to anhydrous substance): Cld: C 44.49 H 6.40 N 9.26 Gd 20.80 Fnd: C 44.28 H 6.55 N 9.11 Gd 20.63

EXAMPLE 9 a) N-(2-Bromopropionyl)-alanine 69.26 g (404 mmol) of α-bromopropionic acid chloride is added in drops at 0° C. to 30 g (336.7 mmol) of alanine and 102.2 g (1010.2 mmol) of triethylamine in 600 ml of methylene chloride. In this case, the temperature remains between 0° C.–5° C. 1000 ml of 5% aqueous hydrochloric acid is added, and the organic phase is separated. The organic phase is extracted once more with 400 ml of 5% aqueous hydrochloric acid, dried on magnesium sulfate and evaporated to dryness in a vacuum. The residue is recrystallized from acetone/diisopropyl ether.

Yield: 52.05 g (69% of theory)

Elementary analysis (relative to anhydrous substance): Cld: C 32.16 H 4.50 N 6.25 Br 35.66 Fnd: C 32.33 H 4.70 N 6.13 Br 35.41 b) 10-(4-Carboxy-1-methyl-2-oxo-3-azapentyl)-1,4,7,10-tetraazacyclododecane-1,4,7-triacetic Acid 38.65 g (111.6 mmol) of 1,4,7-triscarboxymethyl-1,4,7,10-tetraazacyclododecane (=D03A), 108 g (781.2 mmol) of potassium carbonate and 1 g (6 mmol) of potassium iodide are added to 50 g (223.2 mmol) of the title compound of Example 9a, dissolved in 300 ml of acetonitrile/200 ml of water. It is refluxed for 12 hours. It is evaporated to dryness in a vacuum, the residue is taken up in 500 ml of methanol, and then the salts are filtered out. The filtrate is evaporated to dryness, the residue is taken up in 300 ml of water and set at pH 1 with 5N hydrochloric acid. Then purification is done on a column filled with Reillex® 425 PVP. It is eluted with water. The product-containing fractions are evaporated to dryness in a vacuum, and the residue is recrystallized from methanol/acetone.

Yield: 17.72 g (30% of theory) of a colorless solid

Water content: 7.5%

Elementary analysis (relative to anhydrous substance): Cld: C 49.07 H 7.21 N 14.31 Fnd: C 49.23 H 7.38 N 14.15 c) Gadolinium Complex of 10-(4-carboxy-1-methyl-2-oxo-3-azapentyl)-1,4,7,10-tetraazacyclododecane-1,4,7-triacetic Acid 5.55 g (15.32 mmol) of gadolinium oxide is added to 15 g (30.64 mmol) of the title compound of Example 9b, dissolved in 150 ml of water, and it is heated for 3 hours to 90° C. It is evaporated to dryness (vacuum), and the residue is recrystallized from 90% aqueous ethanol. The crystals are suctioned off, washed once with ethanol, then with acetone and finally with diethyl ether and dried in a vacuum furnace at 130° C. (24 hours).

Yield: 18.22 g (90% of theory) of a colorless, crystalline powder

Water content: 2.6%

Elementary analysis (relative to anhydrous substance): Cld: C 37.32 H 5.01 N 10.88 Gd 24.43 Fnd: C 37.13 H 5.20 N 10.61 Gd 24.41

EXAMPLE 10 a) N-(2-Bromopropionyl)-valine 70.2 g (409.7 mmol) of α-bromopropionic acid chloride is added in drops at 0° C. to 40 g (341.4 mmol) of valine and 103.7 g (1024 mmol) of triethylamine in 600 ml of methylene chloride. In this case, the temperature remains between 0° C.–5° C. 1000 ml of 5% aqueous hydrochloric acid is added, and the organic phase is separated. The organic phase is extracted once more with 500 ml of 5% aqueous hydrochloric acid, dried on magnesium sulfate and evaporated to dryness in a vacuum. The residue is recrystallized from acetone/diisopropyl ether.

Yield: 59.39 g (69% of theory)

Elementary analysis (relative to anhydrous substance): Cld: C 38.11 H 5.60 N 5.56 Br 31.69 Fnd: C 38.01 H 5.75 N 5.41 Br 31.48 b) 10-(4-Carboxy-1,5-dimethyl-2-oxo-3-azahexyl)-1,4,7,10-tetraazacyclododecane-1,4,7-triacetic Acid 37.8 g (109.7 mmol) of 1,4,7-triscarboxymethyl-1,4,7,10-tetraazacyclododecane (=D03A), 106.13 g (767.9 mmol) of potassium carbonate and 1 g (6 mmol) of potassium iodide are added to 55 g (218.2 mmol) of the title compound of Example 10a, dissolved in 200 ml of acetonitrile/200 ml of water. It is refluxed for 12 hours. It is evaporated to dryness in a vacuum, the residue is taken up in 500 ml of methanol, and then the salts are filtered out. The filtrate is evaporated to dryness, and the residue is taken up in 300 ml of water and set at pH 1 with 5N hydrochloric acid. Then purification is done on a column filled with Reillex® 425 PVP. It is eluted with water. The product-containing fractions are evaporated to dryness in a vacuum, and the residue is recrystallized from methanol/acetone.

Yield: 17.57 g (29% of theory) of a colorless solid

Water content: 6.3%

Elementary analysis (relative to anhydrous substance):
Cld: C 51.05 H 7.59 N 13.53 Fnd: C 51.18 H 7.70 N 13.39 c) Gadolinium Complex of 10-(4-carboxy-1,5-dimethyl-2-oxo-3-azahexyl]-1,4,7,10-tetraazacyclododecane-1,4,7-triacetic Acid 5.25 g (14.49 mmol) of gadolinium oxide is added to 15 g (28.98 mmol) of the title compound of Example 10b, dissolved in 150 ml of water, and it is heated for 3 hours to 90° C. It is evaporated to dryness (vacuum), and the residue is recrystallized from 90% aqueous ethanol. The crystals are suctioned off, washed once with ethanol, then with acetone and finally with diethyl ether and dried in a vacuum furnace at 130° C. (24 hours).

Yield: 18.57 g (93% of theory) of a colorless, crystalline powder

Water content: 2.5%

Elementary analysis (relative to anhydrous substance):
Cld: C 39.33 H 5.40 N 10.42 Gd 23.41 Fnd: C 39.17 H 5.55 N 10.31 Gd 23.27

EXAMPLE 11 a) N-(2-Bromoacetyl)-glycine-tert-butyl Ester 77.8 g (385.5 mmol) of bromoacetic acid bromide is added in drops at 0° C. to 50 g (296.5 mmol) of glycine-tert-butyl ester hydrochloride salt and 90 g (889.5 mmol) of triethylamine in 500 ml of methylene chloride. In this case, the temperature remains between 0° C.–5° C. 1000 ml of 5% aqueous hydrochloric acid is added, and the organic phase is separated. The organic phase is extracted once more with 500 ml of 5% aqueous hydrochloric acid, dried on magnesium sulfate and evaporated to dryness in a vacuum. The residue is recrystallized from diisopropyl ether/n-hexane.

Yield: 30.5 g (61% of theory)

Elementary analysis: Cld: C 38.11 H 5.60 N 5.56 Br 31.69 Fnd: C 37.92 H 5.76 N 5.38 Br 31.42 b) 10-[4-(tert-Butoxycarbonyl)-2-oxo-3-azabutyl]-1,4,7,10-tetraazacyclododecane-1,4,7-triacetic acid-tri-tert-butyl Ester 200 ml of acetonitrile is added to 20.35 g (80.70 mmol) of the title compound of Example 11a, 25 g (53.8 mmol) of 1,4,7-tris(tert-butoxy-carboxymethyl)-1,4,7,10-tetraazacyclododecane (=D03A-tri-tert-butyl ester), 29.74 g (215.8 mmol) of potassium carbonate and 1 g (6 mmol) of potassium iodide, and it is refluxed for 12 hours. The salts are filtered out, and the filtrate is evaporated to dryness in a vacuum. The residue is dissolved in 800 ml of dichloromethane and extracted twice with 200 ml of 5% aqueous sodium carbonate solution. The organic phase is dried on magnesium sulfate and concentrated by evaporation. After chromatography on silica gel (mobile solvent: dichloromethane/methanol=20:1), 25.09 g of the title compound (68% of theory) is obtained as a colorless foam.

Elementary analysis: Cld: C 59.54 H 9.26 N 10.21 Fnd: C 59.35 H 9.42 N 10.03 c) 10-[4-Carboxy-2-oxo-3-azabutyl]-1,4,7,10-tetraazacyclododecane-1,4,7-triacetic Acid 25 g (36.45 mmol) of the title compound of Example 11b is dissolved in 300 ml of trifluoroacetic acid, and it is stirred for 3 hours at room temperature. It is evaporated to dryness, the residue is taken up in 80 ml of water, and the solution is added to a column, filled with Reillex® 425 PVP. It is eluted with water. The product-containing fractions are combined and evaporated to dryness, and the residue is recrystallized from methanol/acetone.

Yield: 15.24 g (84% of theory) of a colorless, hygroscopic solid

Water content: 7.3%

Elementary analysis (relative to anhydrous substance):
Cld: C 46.85 H 6.77 N 15.18 Fnd: C 46.61 H 6.95 N 15.02 d) Gadolinium Complex of 10-[4-carboxy-2-oxo-3-azabutyl]-1,4,7,10-tetraazacyclododecane-1,4,7-triacetic Acid 5.86 g (16.25 mmol) of gadolinium oxide is added to 15 g (32.50 mmol) of the title compound of Example 11c, dissolved in 200 ml of water, and it is heated for 3 hours to 90° C. It is evaporated to dryness (vacuum), and the residue is recrystallized from 90% aqueous ethanol. The crystals are suctioned off, washed once with ethanol, then with acetone and finally with diethyl ether and dried in a vacuum furnace at 130° C. (24 hours).

Yield: 18.92 g (92% of theory) of a colorless, crystalline powder

Water content: 2.7%

Elementary analysis (relative to anhydrous substance):
Cld: C 35.11 H 4.58 N 11.37 Gd 25.54 Fnd: C 34.92 H 4.71 N 11.14 Gd 25.33

Examples 12–37 below are used to explain the process according to the invention.

Examples 12–24: In situ formation of the metal-complex carboxylic acid mixture that consists of metal-complex carboxylic acid and solubilizing substance:

EXAMPLE 12 a) Bis[2-(benzyloxycarbonylamino)-ethyl]-amine 51.5 g (500 mmol) of diethylenetriamine and 139 ml (1 mol) of triethylamine are dissolved in dichloromethane and mixed at −20° C. with 161 g of benzyl cyanoformate (Fluka) in dichloromethane and then stirred overnight at room temperature. After the reaction is completed, concentration by evaporation is performed during draw-off, the residue is taken up in diethyl ether, the organic phase is washed with sodium carbonate solution and dried with sodium sulfate. The filtrate is mixed with hexane, and the precipitate is filtered off and dried.

Yield: 163.4 g (88% of theory)

Elementary analysis: Cld: C 64.67 H 6.78 N 11.31 Fnd: C 64.58 H 6.83 N 11.28 b) N,N,N',N',N",N"-Hexakis[2-(benzyloxycarbonylamino)-ethyl]trimesic Acid Triamide 13.27 g (50 mmol) of trimesic acid trichloride (Aldrich) and 34.7 ml (250 mmol) of triethylamine are dissolved in dimethylformamide (DMF) and mixed at 0° C. with 65.0 g (175 mmol) of the amine described in Example 12a and then stirred overnight at room temperature. The solution is concentrated by evaporation in a vacuum, and the residue is chromatographed on silica gel with ethyl acetate.

Yield: 39.4 g (62% of theory)

Elementary analysis: Cld: C 65.24 H 5.95 N 9.92 Fnd: C 65.54 H 5.95 N 9.87 c) $N^a,N^\epsilon$-Bis(N,N'-dibenzyloxycarbonyl-lysyl)-lysine, Protected "Tri-lysine"

3.6 g (20 mmol) of lysine-hydrochloride and 6.95 ml (50 mmol) of triethylamine are dissolved in DMF, mixed with 26.8 g (50 mmol) of $N^a$, $N^\epsilon$-dibenzyloxycarbonyl-lysine-p-nitrophenylester (Bachem) and stirred for 2 days at room temperature. After the reaction is completed, it is concentrated by evaporation in a vacuum, and the residue is taken up in ethyl acetate and shaken out with diluted hydrochloric acid. The organic phase is dried with sodium sulfate, the solvent is concentrated by evaporation, and the residue is chromatographed with ethyl acetate/ethanol in a step gradient.

Yield: 10.7 g (57% of theory)

Elementary analysis: Cld: C 63.95 H 6.65 N 8.95 Fnd: C 63.63 H 6.69 N 8.93 d) Completely Protected Benzyloxycarbonyl-24mer-polyamine Based on N,N,N',N',N",N"-hexakis[2-(trilysyl-amino)-ethyl]trimesic Acid Triamide 1.27 g (1 mmol) of the hexa-benzyloxycarbonylamine described in Example 12b is dissolved in glacial acetic acid and mixed with 33% hydrogen bromide in glacial acetic acid while being stirred. After 60 minutes, the incipient precipitation is completed with diethyl ether, the hexaamine-hydrobromide produced is washed with ether, dried in a vacuum and used in the subsequent reaction described below without further purification.

Yield: 0.95 g (quantitative)

7.0 g (7.5 mmol) of the protected "tri-lysine" described in Example 12c, 1.2 g (7.5 mmol) of 1-hydroxybenzotriazole and 2.4 g (7.5 mmol) of 2-(1H-benzotriazol-1-yl)-1,1,3,3-tetramethyluronium tetrafluoroborate (TBTU; Peboc Limited, UK) are dissolved in DMF and stirred for 15 minutes. This solution is then mixed with 5.16 ml (30 mmol) of N-ethyldiisopropylamine and with 0.95 g (1 mmol) of the hexaamine-hydrobromide described above, and it is stirred overnight at room temperature. After the reaction is completed, it is concentrated by evaporation in a vacuum, and the residue is chromatographed on silica gel with ethyl acetate/ethanol (2:1).

Yield: 4.55 g (76% of theory)

Elementary analysis: Cld: C 64.35 H 6.71 N 10.52 Fnd: C 64.08 H 6.57 N 10.29 e) 24-mer-Polyamine based on N,N,N',N',N'',N''-hexakis[2-(trilysyl-amino)-ethyl]-trimesic Acid Triamide, Tetracosahydrochloride 5.99 g (1 mmol) of the 24-mer benzyloxycarbonylamine described in Example 12d above is dissolved in 500 ml of methanol, mixed under nitrogen with 1 g of palladium on activated carbon (10%) and with 24 ml (24 mmol) of 1N HCl and hydrogenated with hydrogen. After the reaction is completed, catalyst is filtered out, and the filtrate is evaporated to dryness.

Yield: 3.65 g (quantitative). Tetracosahydrochloride dissolves in clear form in water.

Elementary analysis: Cld: C 42.48 H 7.71 N 17.28 Cl 23.33 Fnd: C 42.20 H 7.94 N 17.09 Cl 25.06 f) Tetracosakis-amide Conjugate of the 24mer-polyamine Based on N,N,N',N',N'',N''-hexakis[2-(trilysyl-amino)-ethyl]-trimesic Acid Triamide with the Gadolinium Complex of 10-(4-carboxy-1-methyl-2-oxo-3-azabutyl)-1,4,7,10-tetraazacyclododecane-1,4,7-triacetic Acid 31.74 g (50.4 mmol, 3x excess) of the Gd complex of 10-(4-carboxy-1-methyl-2-oxo-3-azabutyl)-1,4,7,10-tetraazacyclododecane- 1,4,7-triacetic acid described in Example 1f, 5.19 g of sodium bromide (50.4 mmol) and 8.7 g (75.6 mmol) of N-hydroxysuccinimide are dissolved in 250 ml of dimethyl sulfoxide at 50° C. After cooling to room temperature, 15.6 g (75.6 mmol) of N,N'-dicyclohexylcarbodiimide is added and preactivated for 60 minutes. A solution of 2.55 g (0.7 mmol) of the tetracosahydrochloride described in Example 12e and 8.5 g of triethylamine in 25 ml of water are added to the N-hydroxysuccinimide ester solution that is thus produced, and it is stirred overnight at room temperature. The suspension that is obtained is then mixed with sufficient acetone until complete precipitation occurs, the precipitate is suctioned off, dried, taken up in water, insoluble dicyclohexylurea is filtered out, and the filtrate is desalinated with an AMICON® YM-3 ultrafiltration membrane (cut off 3,000 Da), and low-molecular components are removed. The retentate is then freeze-dried.

Yield: 11.8 g (88% of theory)
H$_2$O content (Karl-Fischer): 9.0%
Gd determination (AAS): 19.6%
MALDI-TOF mass spectrum: 17.476 (M+Na$^+$)

Elementary analysis (relative to anhydrous substance):
Cld: C 40.26 H 5.35 N 13.24 Gd 21.62 Fnd: C 40.04 H 5.59 N 13.47 Gd 20.88

EXAMPLE 13 a) 1,4,7-Tris[N2,N6-bis(benzyloxycarbonyl)-lysyl]-1,4,7,10-tetraazacyclododecane 49.07 g (95.9 mmol) of di-Z-lysine-N-hydroxysuccinimide ester and 5 g (29 mmol) of cyclene (=1,4,7,10-tetraazacyclododecane) are dissolved in a mixture of 200 ml of toluene/100 ml of dioxane. 9.7 g (95.9 mmol) of triethylamine is added, and it is heated for 12 hours to 70° C. It is evaporated to dryness, the residue is taken up in 600 ml of dichloromethane and extracted 3 times with 200 ml of 5% aqueous potassium carbonate solution each. The organic phase is dried on magnesium sulfate and evaporated to dryness in a vacuum. The residue is chromatographed on silica gel (mobile solvent: ethyl acetate/ethanol=15:1).

Yield: 29.61 g (75% of theory) of a colorless solid

Elementary analysis: Cld: C 65.28 H 6.81 N 10.29 Fnd: C 65.41 H 6.97 N 10.10 b) 1-(4-Carboxybutyryl)-4,7,10-tris(N2,N6-bis(benzyloxycarbonyl)-lysyl]-1,4,7,10-tetraazacyclododecane 3.5 g (30.8 mmol) of glutaric acid anhydride (Fluka) and 6.24 g (61.72 mmol) of triethylamine are added to 28 g (20.56 mmol) of the title compound of Example 13a (dissolved in 200 ml of tetrahydrofuran). It is heated for 6 hours to 50° C. The solution is evaporated to dryness in a vacuum, taken up with 300 ml of dichloromethane and extracted twice with 150 ml of 5% aqueous hydrochloric acid each. The organic phase is dried on magnesium sulfate, evaporated to dryness in a vacuum, and the residue is chromatographed on silica gel (mobile solvent: dichloromethane/methanol=20:1).

Yield: 27.65 g (91% of theory) of a colorless solid

Elementary analysis: Cld: C 64.30 H 6.70 N 9.49 Fnd: C 64.18 H 6.75 N 9.61 c) 1-(4-Nitrophenoxy)-glutaryl)-4,7,10-tris[N2,N6-bis(benzyloxycarbonyl)-lysyl]-1,4,7,10-tetracyclododecane 14.76 g (10 mmol) of the carboxylic acid described in Example 13b and dissolved in 150 ml of dichloromethane is mixed first with 1.53 g (11 mmol) of 4-nitrophenol and then at 0C with 2.27 g (11 mmol) of dicyclohexylcarbodiimide. After stirring overnight at room temperature, dicyclohexylurea is suctioned out, and the filtrate is concentrated by evaporation and reprecipitated from isopropanol. The mother liquor is decanted from the product that accumulates in oily form, the oil in dichloromethane is taken up and concentrated by evaporation in a vacuum. 15.4 g (96.3%) of solid that is rigidified as foam is obtained.

Elementary analysis: Cld: C 63.94 H 6.38 N 9.65 Fnd: C 63.69 H 6.31 N 9.88 d) Completely Protected Benzyloxycarbonyl-36mer-polyamine, Based on an N,N,N',N',N'',N''-hexakis(2-aminoethyl)-trimesic Acid Triamide Core and Six Amine-protected Hexaamine-monocarboxylic Acids Described in Example 13b 1.27 g (1 mmol) of the hexakis-benzyloxycarbonylamine described in Example 12b is dissolved in glacial acetic acid and mixed with 33% hydrogen bromide in glacial acetic acid while being stirred. After 60 minutes, the incipient precipitation is completed with diethyl ether, the hexa-amine-hexa-hydrobromide that is produced is washed with ether, dried in a vacuum and further reacted without additional purification.

Yield: 0.95 g (quantitative)

Then, the hexa-amine-hexa-hydrobromide is dissolved in 150 ml of DMF, mixed with 15.99 g (10 mmol) of the 4-nitrophenyl active ester described in Example 13c and with 4.05 g (40 mmol) of triethylamine, stirred overnight at room temperature and finally evaporated to dryness in a vacuum. The residue is taken up in ethyl acetate and washed in succession with water, diluted sodium hydroxide solution and saturated NaCl solution. The organic phase is dried on sodium sulfate, and the filtrate is evaporated to dryness, and the residue is chromatographed on silica gel (mobile solvent: dichloromethane/methanol 18:2).

Yield: 6.55 g (71% of theory) of a colorless solid

Elementary analysis: Cld: C 64.54 H 6.73 N 10.49 Fnd: C 64.37 H 6.91 N 10.74

MALDI-TOF mass spectrum: molar peak at 9235 (M+Na$^+$)

e) Hexatriacontakis-amide Conjugate of the 36mer-polyamine of Example 13d with the Dysprosium Complex of 10-(4-carboxy-1-methyl-2-oxo-3-azabutyl)-1,4,7,10-tetraazacyclododecane-1,4,7-triacetic Acid 1.84 (0.2 mmol) of the 36mer-benzyloxycarbonylamine described in Example 13d is dissolved in glacial acetic acid and mixed with 33% hydrogen bromide in glacial acetic acid while being stirred. After 5 hours, the incipient precipitation is completed with diethyl ether, the 36mer-amine-hydrobromide that is produced is washed with ether, dried in a vacuum and used in the reaction described below without additional purification.

Yield: 1.5 g (quantitative)

13.6 g (21.6 mmol, 3× excess) of the dysprosium complex of 10-(4-carboxy-1-methyl-2-oxo-3-azabutyl)-1,4,7,10-tetraazacyclododecane-1,4,7-triacetic acid, described in Example 2, and 3.73 g (32.4 mmol) of N-hydroxysuccinimide are dissolved in 100 ml of dimethyl sulfoxide at 90° C. After cooling to room temperature, 6.7 g (32.4 mmol) of N,N'-dicyclohexylcarbodiimide is added and preactivated for 60 minutes. A solution of 1.5 g (0.2 mmol) of the above-described hexatriaconta-hydrobromide and 3.5 g of triethylamine in 10 ml of water is added to the N-hydroxysuccinimide ester solution that is thus produced, and it is stirred overnight at room temperature. The suspension that is obtained is then mixed with sufficient acetone until complete precipitation occurs, the precipitate is suctioned off, dried, taken up in water, insoluble dicyclohexylurea is filtered out, and the filtrate is desalinated with an AMICON® YM-3 ultrafiltration membrane (cut off 3,000 Da), and low-molecular components are removed. The retentate is then freeze-dried.

Yield: 4.7 g (79% of theory)

H$_2$O content (Karl-Fischer): 10.5%

Dy determination (AAS): 19.7%

MALDI-TOF mass spectrum: 26.616 (M+Na$^+$)

Elementary analysis (relative to anhydrous substance): Cld: C 40.24 H 5.35 N 13.11 Dy 22.00 Fnd: C 39.97 H 5.46 N 12.90 Dy 21.29

EXAMPLE 14

Polyamide Conjugate of Poly-lysine with the Gadolinium Complex of 10-(4-carboxy-1-methyl-2-oxo-3-azabutyl)-1,4,7,10-tetraazacyclododecane-1,4,7-triacetic Acid 3.15 g (5 mmol) of the Gd complex that is described in Example 1f and 0.58 g (5 mmol) of N-hydroxysuccinimide are dissolved in 25 ml of dimethyl sulfoxide while being heated. After cooling to room temperature, 1.03 g (5 mmol) of N,N'-dicyclohexylcarbodiimide is added, and it is stirred for 60 minutes. A solution of 523 mg (2.5 mmol) of poly-lysine-hydrobromide (Sigma) and 506 mg (5 mmol) of triethylamine in 5 ml of water are added to the N-hydroxysuccinimide ester solution that is thus produced, and it is stirred overnight at room temperature. The suspension that is obtained is then mixed with sufficient acetone until complete precipitation occurs, the precipitate is suctioned off, dried, taken up in water, insoluble dicyclohexylurea is filtered out, and the filtrate is desalinated with an AMICON® YM-3 ultrafiltration membrane (cut off 3000 Da), and low-molecular components are removed. The retentate is then freeze-dried.

Yield: 1.8 g (82% of theory)

H$_2$O content (Karl-Fischer): 10.2%

Gd determination (AAS): 19.0%

Elementary analysis (relative to anhydrous substance): Cld: C 40.58 H 5.45 N 13.25 Gd 21.25 Fnd: C 40.81 H 5.21 N 13.44 Gd 20.87

EXAMPLE 15

Dotriacontakis-amide Conjugate of the 32mer-dendrimer-amine "DAB(PA)$_4$(PA)$_8$(PA)$_{16}$(PA)$_{32}$" and the Dysprosium Complex of 10-(4-carboxy-1-ethyl-2-oxo-3-azabutyl)-1,4,7,10-tetraazacyclododecane-1,4,7-triacetic Acid 3.25 g (5 mmol) of the Dy complex of 10-(4-carboxy-1-ethyl-2-oxo-3-azabutyl)-1,4,7,10-tetraazacyclododecane-1,4,7-triacetic acid described in Example 5 and 0.58 g (5 mmol) of N-hydroxysuccinimide are dissolved in 25 ml of dimethyl sulfoxide while being heated. After cooling to room temperature, 1.03 g (5 mmol) of N,N'-dicyclohexylcarbodiimide is added, and it is stirred for one hour. 275 mg (0.078 mmol) of the 32mer-dendrimer-amine described in Example VIII of WO 93/14147 and 506 mg (5 mmol) of triethylamine in 5 ml of water are added to the N-hydroxysuccinimide ester solution that is thus produced, and it is stirred overnight at room temperature. The suspension that is obtained is then mixed with sufficient acetone until complete precipitation occurs, the precipitate is suctioned off, dried, taken up in water, insoluble dicyclohexylurea is filtered out, and the filtrate is desalinated with an AMICON® YM-3 ultrafiltration membrane (cut off 3000 Da), and low-molecular components are removed. The retentate is then freeze-dried.

Yield: 1.62 g (82.7% of theory)

H$_2$O content (Karl-Fischer): 7.3%

Dy determination (AAS): 20.5%

Elementary analysis (relative to anhydrous substance): Cld: C 40.90 H 5.76 N 13.37 Dy 22.36 Fnd: C 40.55 H 6.07 N 13.69 Dy 21.83

EXAMPLE 16

Amide Conjugate of Daunomycin with the Gadolinium Complex of 1-[1-methyl-2-oxo-3-aza-4-carboxybutyl]-4,7,10-tris(carboxymethyl)-1,4,7,10-tetraazacyclododecane 1 g (1.588 mmol) of the gadolinium complex of 1-[1-methyl-2-oxo-3-aza-4-carboxybutyl]-4,7,10-tris(carboxymethyl)-1,4,7,10-tetraazacyclododecane, 134.6 mg (3.176 mmol) of lithium chloride and 365.8 mg (3.176 mmol) of N-hydroxysuccinimide are dissolved in 10 ml of dimethyl sulfoxide while being heated slightly and then cooled to 10° C. 393 mg (1.906 mmol) of dicyclohexylcarbodiimide is added at 10° C., and it is stirred for 45 minutes at room temperature. 812.3 mg (1.588 mmol) of daunomycin, dissolved in 5 ml of dimethyl sulfoxide, and then 321.4 mg (3.176 (mol) of triethylamine are added to the N-hydroxysuccinimide ester solution that is thus produced. It is stirred overnight at room temperature. 200 ml of acetone is added in drops to the suspension that is obtained, the precipitate is filtered out, and it is rewashed twice with some acetone. The residue is purified by column chromatography (RP18/mobile solvent: gradient consisting of water/acetonitrile/tetrahydrofuran).

Yield: 1.76 g (85% of theory) of a colorless, flocculent powder after freeze-drying Water content: 6.3%

Elementary analysis (relative to anhydrous substance): Cld: C 49.19 H 5.11 N 7.48 Gd 14.00 Fnd: C 49.03 H 5.27 N 7.31 Gd 13.82

EXAMPLE 17

Amide Conjugate of Adriamycin with the Gadolinium Complex of 1-[1-methyl-2-oxo-3-aza-4-carboxybutyl]-4,7,10-tris(carboxymethyl)-1,4,7,10-tetraazacyclododecane 1 g (1.588 mmol) of the gadolinium complex of 1-[1-methyl-2-oxo-3-aza-4-carboxybutyl]-4,7,10-tris(carboxymethyl)-1,4,7,10-tetraazacyclododecane, 134.6 mg (3.176 mmol) of lithium chloride and 365.8 mg (3.176 mmol) of N-hydroxysuccinimide are dissolved in 10 ml of dimethyl sulfoxide while being heated slightly and then cooled to 10° C. 393 mg (1.906 mmol) of dicyclohexylcarbodiimide is added at 10° C., and it is stirred for 45 minutes at room temperature. 812.3 mg (1.588 mmol) of adriamycin, dissolved in 5 ml of dimethyl sulfoxide, and then 321.4 mg (3.176 mmol) of triethylamine are added to the N-hydroxysuccinimide ester solution that is thus produced. It is stirred overnight at room temperature. 200 ml of acetone is added in drops to the suspension that is obtained, the precipitate is filtered out, and it is rewashed twice with some acetone. The residue is purified by column chromatography (RP18/mobile solvent: gradient consisting of water/acetonitrile/tetrahydrofuran).

Yield: 1.84 g (87% of theory) of a colorless, flocculent powder after freeze-drying Water content: 7.2%

Elementary analysis (relative to anhydrous substance): Cld: C 48.50 H 5.04 N 7.38 Gd 13.80 Fnd: C 48.37 H 5.18 N 7.21 Gd 13.60

EXAMPLE 18

Polyamide Conjugate of Human Serum Albumin with the Gadolinium Complex of 10-(5-carboxy-1-methyl-2-oxo-3-azapentyl)-1,4,7,10-tetraazacyclododecane-1,4,7-triacetic Acid 3.22 g (5 mmol) of the gadolinium complex of 10-(5-carboxy-1-methyl-2-oxo-3-azapentyl)-1,4,7,10-tetraazacyclododecane-1,4,7-triacetic acid (Example 7c), 868 mg (10 mmol) of lithium bromide and 1.15 g (10 mmol) of N-hydroxysuccinimide are dissolved in 30 ml of dimethyl sulfoxide while being heated slightly and then cooled to 10° C. 1.24 g (6 mmol) of dicyclohexylcarbodiimide is added at 10° C., and it is stirred for 8 hours at room temperature. The N-hydroxysuccinimide ester solution that is thus produced is cooled again to 10° C. and is added at 10° C. to a suspension of 6.6 g of human serum albumin (Sigma), which is set at about pH 10 by adding 5 ml of 1N sodium hydroxide solution, and it is stirred overnight at this temperature. The suspension that is obtained is then mixed with sufficient acetone until complete precipitation occurs, the precipitate is suctioned off, dried, taken up in water, insoluble dicyclohexylurea is filtered out, and the filtrate is desalinated with an AMICON® YM-10 ultrafiltration membrane (cut off 10,000 Da), and low-molecular components are removed. The retentate is then freeze-dried. A colorless powder is obtained.

Yield: 7.9 g (89% of theory, relative to a conjugate with 21 Gd complexes)

$H_2O$ content (Karl-Fischer): 10.12%

Gd determination (AAS): 3.77%

Elementary analysis (relative to the anhydrous substance of an $HSA(Gd)_{21}$ conjugate): Cld: Gd 4.15 Fnd: Gd 4.09

EXAMPLE 19

Hexaamide Conjugate of 6,6',6'',6''',6'''',6'''''-hexaamino-6,6',6'',6''',6'''',6'''''-hexadeoxy-α-cyclodextrin with the Gadolinium Complex of 10-(13-carboxy-1-methyl-2-oxo-3-azatridecyl)-1,4,7,10-tetraazacyclododecane-1,4,7-triacetic Acid 3.78 g (5 mmol) of the gadolinium complex of 10-(5-carboxy-1-methyl-2-oxo-3-azatridecyl)-1,4,7,10-tetraazacyclododecane-1,4,7-triacetic acid (Example 8c), 868 mg (10 mmol) of lithium bromide and 1.15 g (10 mmol) of N-hydroxysuccinimide are dissolved in 30 ml of dimethyl sulfoxide while being heated slightly and then cooled to 10° C. 1.24 g (6 mmol) of dicyclohexylcarbodiimide is added at 10° C., and it is stirred for 8 hours at room temperature. The N-hydroxysuccinimide ester solution that is thus produced is added to a suspension of 315 mg (0.25 mmol) of 6,6',6'',6''',6'''',6'''''-hexaamino-6,6',6'',6''',6'''',6'''''-hexadeoxy-α-cyclodextrin [J. Boger, R. J. Corcoran and J.-M. Lehn, Helv. Chim. Acta 61, 2190–2218 (1978)] in dimethyl sulfoxide, and it is stirred overnight at this temperature. The suspension that is obtained is then mixed with sufficient acetone until complete precipitation occurs, the precipitate is suctioned off, dried, taken up in water, insoluble dicyclohexylurea is filtered out, and the filtrate is desalinated with an AMICON® YM-3 ultrafiltration membrane (cut off 3,000 Da), and low-molecular components are removed. The retentate is then freeze-dried. A colorless powder is obtained.

Yield: 1.34 g (89.9% of theory)

$H_2O$ content (Karl-Fischer): 9.5%

Gd determination (AAS): 16.4%

Elementary analysis (relative to anhydrous substance): Cld: C 45.42 H 6.39 N 9.35 Gd 17.49 Fnd: C 45.25 H 6.14 N 9.69 Gd 17.04

EXAMPLE 20

Amide Conjugate of 3'-amino-3'-deoxyguanosine with the Gadolinium Complex of 1-[1-methyl-2-oxo-3-aza-4-carboxybutyl]-4,7,10-tris(carboxymethyl)-1,4,7,10-tetraazacyclododecane 1 g (1.588 mmol) of the gadolinium complex of 1-[1-methyl-2-oxo-3-aza-4-carboxybutyl]-4,7,10-tris(carboxymethyl)-1,4,7,10-tetraazacyclododecane, 476 mg (3.176 mmol) of sodium iodide and 365.8 mg (3.176 mmol) of N-hydroxysuccinimide are dissolved in 10 ml of dimethyl sulfoxide while being heated slightly and then cooled to 10° C. 393 mg (1.906 mmol) of dicyclohexylcarbodiimide is added at 10° C., and it is stirred for 45 minutes at room temperature. 422.8 mg (1.588 mmol) of 3'-amino-3'- deoxyguanosine, dissolved in 5 ml of dimethyl sulfoxide, and then 321.4 mg (3.176 mmol) of triethylamine are added to the N-hydroxysuccinimide ester solution that is thus produced. It is stirred overnight at room temperature. 200 ml of acetone is added in drops to this solution, the precipitate is filtered off, and it is rewashed twice with some acetone. The residue is purified by column chromatography (RP18/mobile solvent: gradient consisting of water/acetonitrile/tetrahydrofuran).

Yield: 1.30 g (88% of theory) of a colorless, flocculent powder after freeze-drying.

Water content: 5.3%

Elementary analysis (relative to anhydrous substance): Cld: C 39.67 H 4.82 N 17.55 Gd 17.91 Fnd: C 39.54 H 4.97 N 17.43 Gd 17.82

EXAMPLE 21

Amide Conjugate of Dehydroabiethylamine with the Gadolinium Complex of 1-[1-methyl-2-oxo-3-aza-4-carboxybutyl]-4,7,10-tris(carboxymethyl)-1,4,7,10-tetraazacyclododecane 1 g (1.588 mmol) of the gadolinium complex of 1-[1-methyl-2-oxo-3-aza-4-carboxybutyl]-4,7,10-tris(carboxymethyl)-1,4,7,10-tetraazacyclododecane, 134.6 mg (3.176 mmol) of lithium chloride and 442 mg (3.176 mmol) of 4-nitrophenol are dissolved in 10 ml of dimethyl sulfoxide while being heated slightly and then cooled to 10° C. 393 mg (1.906 mmol) of dicyclohexylcarbodiimide is added at 10° C., and it is stirred for 45 minutes at room temperature. 422.8 mg (1.588 mmol) of dehydroabiethylamine, dissolved in 5 ml of dimethyl sulfoxide, and then 321.4 mg (3.176 mmol) of triethylamine are added to the solution that is thus produced. It is stirred overnight at room temperature. 100 ml of acetone is added in drops to this solution, the precipitate is filtered off, and it is rewashed twice with some acetone. The residue is purified by column chromatography (RP18/mobile solvent: gradient consisting of water/acetonitrile/tetrahydrofuran).

Yield: 1.36 g (91% of theory) of a vitreous solid after freeze-drying

Water content: 4.5%

Elementary analysis (relative to anhydrous substance): Cld: C 52.21 H 6.63 N 9.37 Gd 17.53 Fnd: C 52.10 H 6.70 N 9.25 Gd 17.41

EXAMPLE 22

Amide Conjugate of Ampicillin with the Gadolinium Complex of 1-[1-methyl-2-oxo-3-aza-4-carboxybutyl]-4,7,10-tris(carboxymethyl)-1,4,7,10-tetraazacyclododecane 1 g (1.588 mmol) of the gadolinium complex of 1-[1-methyl-2-oxo-3-aza-4-carboxybutyl]-4,7,10-tris(carboxymethyl)-1,4,7,10-tetraazacyclododecane, 134.6 mg (3.176 mmol) of lithium chloride and 442 mg (3.176 mmol) of 4-nitrophenol are dissolved in 10 ml of dimethyl sulfoxide while being heated slightly and then cooled to 10° C. 393 g (1.906 mmol) of dicyclohexylcarbodiimide is added at 10° C., and it is stirred for 45 minutes at room temperature. 554.9 mg (1.588 mmol) of ampicillin, dissolved in 5 ml of dimethyl sulfoxide, and then 482 mg (4.764 mmol) of triethylamine are added to the solution that is thus produced. It is stirred overnight at room temperature. 100 ml of acetone is added in drops to this solution, the precipitate is filtered off, and it is rewashed twice with some acetone. The residue is purified by column chromatography (RP18/mobile solvent: gradient consisting of water/acetonitrile/tetrahydrofuran/0.5% trifluoroacetic acid).

Yield: 1.46 g (87% of theory) of a colorless, flocculent powder after freeze-drying Water content: 8.1%

Elementary analysis (relative to anhydrous substance): Cld: C 45.76 H 4.88 N 10.10 S 3.30 Gd 16.19 Fnd: C 45.65 H 5.01 N 10.02 S 3.19 Gd 16.03

EXAMPLE 23

Amide Conjugate of Pentapeptide $NH_2$-Val-Leu-Phe-Phe-Ala-OH with the Gadolinium Complex of 1-[1-methyl-2-oxo-3-aza-4-carboxybutyl]-4,7,10-tris(carboxymethyl)-1,4,7,10-tetraazacyclododecane 1 g (1.588 mmol) of the gadolinium complex of 1-[1-methyl-2-oxo-3-aza-4-carboxybutyl]-4,7,10-tris(carboxymethyl)-1,4,7,10-tetraazacyclododecane, 134.6 mg (3.176 mmol) of lithium chloride and 365.8 mg (3.176 mmol) of N-hydroxysuccinimide are dissolved in 10 ml of dimethyl sulfoxide while being heated slightly and then cooled to 10° C. 393 mg (1.906 mmol) of dicyclohexylcarbodiimide is added at 10° C., and it is stirred for 45 minutes at room temperature. 946 mg (1.588 mmol) of the pentapeptide $NH_2$-Val-Leu-Phe-Phe-Ala-OH (produced according to the solid-phase technique), dissolved in 5 ml of dimethyl sulfoxide, and then 321.4 mg (3.176 mmol) of triethylamine are added to the N-hydroxysuccinimide ester solution that is thus produced. It is stirred overnight at room temperature. 200 ml of acetone is added in drops to this solution, the precipitate is filtered off, and it is rewashed twice with some acetone. The residue is purified by column chromatography (RP18/mobile solvent: gradient consisting of water/acetonitrile/tetrahydrofuran).

Yield: 1.74 g (85% of theory) of a colorless, flocculent powder after freeze-drying Water content: 6.5%

Elementary analysis (relative to anhydrous substance): Cld: C 50.73 H 6.09 N 11.60 Gd 13.02 Fnd: C 50.58 H 6.21 N 11.48 Gd 12.86

EXAMPLE 24

Amide Conjugate of N-methylglucosamine with the Gadolinium Complex of 1-[1-methyl-2-oxo-3-aza-4-carboxybutyl]-4,7,10-tris(carboxymethyl)-1,4,7,10-tetraazacyclododecane 1 g (1.588 mmol) of the gadolinium complex of 1-[1-methyl-2-oxo-3-aza-4-carboxybutyl]-4,7,10-tris(carboxymethyl)-1,4,7,10-tetraazacyclododecane and 134.6 mg (3.176 mmol) of lithium chloride are dissolved in 10 ml of dimethyl sulfoxide while being heated slightly and then cooled to 10° C. 310 mg (1.588 mmol) of D(−)-N-methylglucosamine and 785.4 mg (3.176 mmol) of 2-ethoxy-1-ethoxycarbonyl-1,2-dihydroquinoline (EEDQ) are added at 10° C. It is stirred overnight at room temperature. 200 ml of acetone is added in drops to this solution, the precipitate is filtered off, and it is rewashed twice with some acetone. The residue is purified by column chromatography (RP18/mobile solvent: gradient consisting of water/acetonitrile/tetrahydrofuran).

Yield: 1.25 g (91% of theory) of a colorless, flocculent powder after freeze-drying Water content: 6.7%

Elementary analysis (relative to anhydrous substance):
Cld: C 38.70 H 5.62 N 10.41 Gd 19.49 Fnd: C 38.60 H 5.73 N 10.28 Gd 19.35

Examples 25–37: Isolation of the Metal-complex Carboxylic Acid Mixture that Consists of Metal-complex Carboxylic Acid and Solubilizing Substance

EXAMPLE 25 a) Mixture that Consists of the Gadolinium Complex of 10-(4-carboxy-1-methyl-2-oxo-3-azabutyl)-1,4,7,10-tetraazacyclododecane-1,4,7-triacetic Acid and 2 Molar Equivalents of Lithium Chloride 31.74 g (50.4 mmol) of the Gd complex of 10-(4-carboxy-1-methyl-2-oxo-3-azabutyl)-1,4,7,10-tetraazacyclododecane-1,4,7-triacetic acid described in Example 1f is dissolved in 200 ml of water and mixed with 4.27 g (100.8 mmol) of lithium chloride. The clear solution is then freeze-dried and finally further dried in a vacuum overnight at 100° C. A colorless powder is obtained.

Yield: 36.0 g (quantitative)
$H_2O$ content (Karl-Fischer): 3.5%
Gd determination (AAS): 21.2%
Elementary analysis (relative to anhydrous substance):
Cld: C 31.94 H 4.23 N 9.80 Gd 22.01 Li 1.94 Cl 9.92 Fnd: C 31.72 H 4.44 N 9.57 Gd 21.69 Li 1.98 Cl 9.70 b) Tetracosakis-amide Conjugate of the 24mer-polyamine Based on N,N,N',N',N",N"-hexakis[2-(trilysyl-amino)-ethyl]-trimesic Acid Triamide with the Gadolinium Complex of 10-(4-carboxy-1-methyl-2-oxo-3-azabutyl)-1,4,7,10-tetracyclododecane-1,4,7-triacetic Acid 36.0 g (50.4 mmol, 3x excess) of the lithium mixed salt with the Gd complex of 10-(4-carboxy-1-methyl-2-oxo-3-azabutyl)-1,4,7,10-tetraazacyclododecane-1,4,7-triacetic acid described in Example 25a above and 8.7 g (75.6 mmol) of N-hydroxysuccinimide are dissolved in 250 ml of dimethyl sulfoxide at room temperature. Then, 15.6 g (75.6 mmol) of N,N'-dicyclohexylcarbodiimide is added and pre-activated for 60 minutes. A solution of 2.55 g (0.7 mmol) of the tetracosahydrochloride described in Example 12e and 8.5 g of triethylamine in 25 ml of water are added to the N-hydroxysuccinimide ester solution that is thus produced, and it is stirred overnight at room temperature. The suspension that is obtained is then mixed with sufficient acetone until complete precipitation occurs, the precipitate is suctioned off, dried, taken up in water, insoluble dicyclohexylurea is filtered out, and the filtrate is desalinated with an AMICON® YM-3 ultrafiltration membrane (cut off 3,000 Da), and low-molecular components are removed. The retentate is then freeze-dried.

Yield: 11.8 g (88% of theory)
$H_2O$ content (Karl-Fischer): 9.1%
Gd determination (AAS): 19.4%
MALDI-TOF mass spectrum: 17.476 (M+Na$^+$)
Elementary analysis (relative to anhydrous substance):
Cld: C 40.26 H 5.35 N 13.24 Gd 21.62 Fnd: C 40.10 H 5.51 N 13.52 Gd 20.98

EXAMPLE 26 a) Mixture that Consists of the Gadolinium Complex of 10-(4-carboxy-1-methyl-2-oxo-3-azabutyl)-1,4,7,10-tetraazacyclododecane-1,4,7-triacetic Acid and 1 Molar Equivalent of Sodium Bromide 31.74 g (50.4 mmol) of the Gd complex of 10-(4-carboxy-1-methyl-2-oxo-3-azabutyl)-1,4,7,10-tetraazacyclododecane-1,4,7-triacetic acid described in Example 1f is dissolved in 200 ml of water and mixed with 5.19 g (50.4 mmol) of sodium bromide. The clear solution is then freeze-dried and finally further dried in a vacuum overnight at 100° C. A colorless powder is obtained.

Yield: 36.9 g (quantitative)
$H_2O$ content (Karl-Fischer): 3.7%
Gd determination (AAS): 20.9%
Elementary analysis (relative to anhydrous substance):
Cld: C 31.15 H 4.13 N 9.56 Gd 21.46 Na 3.14 Br 10.91 Fnd: C 30.95 H 4.20 N 9.66 Gd 21.13 Na 3.31 Br 10.54 b) Hexatriacontakis-amide Conjugate of the 36mer-polyamine of Example 13d with the Gadolinium Complex of 10-(4-carboxy-1-methyl-2-oxo-3-azabutyl)-1,4,7,10-tetraazacyclododecane-1,4,7-triacetic Acid 1.84 (0.2 mmol) of the 36mer-benzyloxycarbonylamine described in Example 13d is dissolved in glacial acetic acid and mixed with 33% hydrogen bromide in glacial acetic acid while being stirred. After 5 hours, the incipient precipitation is completed with diethyl ether, and the 36mer-amine-hydrobromide that is produced is washed with ether, dried in a vacuum and used in the reaction described below without additional purification.

Yield: 1.5 g (quantitative)

15.8 g (21.6 mmol, 3x excess) of the sodium bromide mixed salt, described in Example 26a above, with the Gd complex of 10-(4-carboxy-1-methyl-2-oxo-3-azabutyl)-1,4, 7,10-tetraazacyclododecane-1,4,7-triacetic acid and 3.73 g (32.4 mmol) of N-hydroxysuccinimide is dissolved in 100 ml of dimethyl sulfoxide. Then, 6.7 g (32.4 mmol) of N,N'-dicyclohexylcarbodiimide is added and preactivated for 60 minutes. A solution of 1.5 g (0.2 mmol) of the above-described hexatriaconta-hydrobromide and 3.5 g of triethylamine in 10 ml of water is added to the N-hydroxysuccinimide ester solution that is thus produced, and it is stirred overnight at room temperature. The suspension that is obtained is then mixed with sufficient acetone until complete precipitation occurs, the precipitate is suctioned off, dried, taken up in water, insoluble dicyclohexylurea is filtered out, and the filtrate is desalinated with an AMICON® YM-3 ultrafiltration membrane (cut off 3,000 Da), and low-molecular components are removed. The retentate is then freeze-dried.

Yield: 4.8 g (82% of theory)
$H_2O$ content (Karl-Fischer): 9.9%
Gd determination (AAS): 18.6%
MALDI-TOF mass spectrum: 26.428 (M+Na$^+$)
Elementary analysis (relative to anhydrous substance):
Cld: C 40.53 H 5.37 N 13.21 Gd 21.44 Fnd: C 39.46 H 5.46 N 12.97 Gd 21.01

EXAMPLE 27

Polyamide Conjugate of Poly-lysine with the Gadolinium Complex of 10-(4-carboxy-1-methyl-2-oxo-3-azabutyl)-1,4,7,10-tetraazacyclododecane-1,4, 7-triacetic Acid 3.57 g (5 mmol) of the lithium mixed salt, described in Example 25a, with the Gd complex of 10-(4-carboxy-1-methyl-2-oxo-3-azabutyl)-1,4,7,10-tetraazacyclododecane-1,4,7-triacetic acid and 0.58 g (5 mmol) of N-hydroxysuccinimide is dissolved in 25 ml of dimethyl sulfoxide, and 1.03 g (5 mmol) of N,N'-dicyclohexylcarbodiimide is added and stirred for 60 minutes. A solution of 523 mg (2.5 mmol) of poly-lysine-hydrobromide (Sigma) and 506 mg (5 mmol) of triethylamine in 5 ml of water is added to the N-hydroxysuccinimide ester solution that is thus produced, and it is stirred overnight at room temperature. The suspension that is obtained is then mixed with sufficient acetone until complete precipitation occurs, the precipitate is suctioned off, dried, taken up in water, insoluble dicyclohexylurea is filtered out, and the filtrate is desalinated with an AMICON® YM-3 ultrafiltration membrane (cut off 3,000 Da), and low-molecular components are removed. The retentate is then freeze-dried.

Yield: 1.7 g (82% of theory)
$H_2O$ content (Karl-Fischer): 9.9%
Gd determination (AAS): 19.3%
Elementary analysis (relative to anhydrous substance):
Cld: C 40.58 H 5.45 N 13.25 Gd 21.25 Fnd: C 40.67 H 5.25 N 13.52 Gd 20.64

EXAMPLE 28 a) Mixture that Consists of the Dysprosium Complex of 10-(4-carboxy-1-ethyl-2-oxo-3-azabutyl)-1,4,7,10-tetraazacyclododecane-1, 4, 7-triacetic Acid and One Molar Equivalent of Sodium Bromide 32.71 g (50.4 mmol) of the Dy complex of 10-(4-carboxy-1-ethyl-2-oxo-3-azabutyl) -1,4,7,10-tetraazacyclododecane-1,4,7-triacetic acid described in Example 5 is dissolved in 200 ml of water and mixed with 5.19 g (50.4 mmol) of sodium bromide. The clear solution is then freeze-dried and finally further dried in a vacuum overnight at 100° C. A colorless powder is obtained.

Yield: 37.9 g (quantitative)
$H_2O$ content (Karl-Fischer): 3.5%
Dy determination (AAS): 20.7%
Elementary analysis (relative to anhydrous substance):
Cld: C 31.95 H 4.29 N 9.31 Dy 21.61 Na 3.06 Br 10.63 Fnd: C 31.70 H 4.44 N 9.08 Dy 21.09 Na 3.24 Br 10.96 b) Dotriacontakis-amide Conjugate from the 32mer Dendrimer-amine "DAB(PA)$_4$(PA)$_8$(PA)$_{16}$(PA)$_{32}$" and the Dysprosium Complex of 10-(4-carboxy-1-ethyl-2-oxo-3-azabutyl)-1,4,7,10-tetraazacyclododecane-1,4,7-triacetic Acid 3.76 g (5 mmol) of the sodium bromide mixed salt, described in Example 28a above, with the Dy complex of 10-(4-carboxy-1-ethyl-2-oxo-3-azabutyl)-1,4,7,10-tetraazacyclo-dodecane-1,4,7-triacetic acid, 696 mg (5 mmol) of 4-nitrophenol and 1.03 g (5 mmol) of N,N'-dicyclohexylcarbodiimide is dissolved in 25 ml of dimethyl sulfoxide, and it is stirred for one hour. 275 mg (0.078 mmol) of the 32mer-dendrimer-amine described in Example VIII of WO 93/14147 and 506 mg (5 mmol) of triethylamine in 5 ml of water are added to the activated ester solution that is thus produced, and it is stirred overnight at room temperature. The suspension that is obtained is then mixed with sufficient acetone until complete precipitation occurs, the precipitate is suctioned off, dried, taken up in water, insoluble dicyclohexylurea is filtered out, and the filtrate is desalinated with an AMICON® YM-3 ultrafiltration membrane (cut off 3,000 Da), and low-molecular components are removed. The retentate is then freeze-dried.

Yield: 1.62 g (83% of theory)
$H_2O$ content (Karl-Fischer): 10.0%
Dy determination (AAS): 20.3%
Elementary analysis (relative to anhydrous substance):
Cld: C 40.90 H 5.76 N 13.37 Dy 22.36 Fnd: C 40.59 H 5.98 N 13.24 Dy 21.91

EXAMPLE 29

Amide Conjugate of Daunomycin with the Gadolinium Complex of 1-[1-methyl-2-oxo-3-aza-4-carboxybutyl]-4,7,10-tris(carboxymethyl)-1,4,7,10-tetraazacyclododecane 1.135 g (1.588 mmol) of the title compound of Example 25a and 365.8 mg (3.176 mmol) of 4-nitrophenol are dissolved in 10 ml of dimethyl sulfoxide and then cooled to 10° C. 393 mg (1.906 mmol) of dicyclohexylcarbodiimide is added at 10° C., and it is stirred for 45 minutes at room temperature. 812.3 mg (1.588 mmol) of daunomycin, dissolved in 5 ml of dimethyl sulfoxide, then 321.4 mg (3.176 mmol) of triethylamine are added to the suspension that is thus produced. It is stirred overnight at room temperature. 200 ml of acetone is added in drops to the suspension that is obtained, the precipitate is filtered off, and it is rewashed twice with some acetone. The residue is purified by column chromatography (RP18/mobile solvent: gradient that consists of water/acetonitrile/tetrahydrofuran).

Yield: 1.81 g (87% of theory) of a colorless, flocculent powder after freeze-drying Water content: 6.8%

Elementary analysis (relative to anhydrous substance):
Cld: C 49.19 H 5.11 N 7.48 Gd 14.00 Fnd: C 49.01 H 5.20 N 7.34 Gd 13.90

EXAMPLE 30

Amide Conjugate of Adriamycin with the Gadolinium Complex of 1-[1-methyl-2-oxo-3-aza-4-carboxybutyl]-4,7,10-tris(carboxymethyl)-1,4,7,10-tetracyclododecane 1.135 g (1.588 mmol) of the title compound of Example 25a and 442 mg (3.176 mmol) of 4-nitrophenol are dissolved in 10 ml of dimethyl sulfoxide and then cooled to 10° C. 393 mg (1.906 mmol) of dicyclohexylcarbodiimide is added at 10° C., and it is stirred for 45 minutes at room temperature. 812.3 mg (1.588 mmol) of adriamycin, dissolved in 5 ml of dimethyl sulfoxide, then 321.4 mg (3.176 mmol) of triethylamine are added to the suspension that is thus produced. It is stirred overnight at room temperature. 200 ml of acetone is added in drops to the suspension that is obtained, the precipitate is filtered off, and it is rewashed twice with some acetone. The residue is purified by column chromatography (RP18/mobile solvent: gradient that consists of water/acetonitrile/tetrahydrofuran).

Yield: 1.94 g (90% of theory) of a colorless, flocculent powder after freeze-drying Water content: 9.1%

Elementary analysis (relative to anhydrous substance):
Cld: C 48.50 H 5.04 N 7.38 Gd 13.80 Fnd: C 48.35 H 5.21 N 7.24 Gd 13.63

EXAMPLE 31 a) Mixture that Consists of the Dysprosium Complex of 10-(4-carboxy-1-methyl-2-oxo-3-azabutyl)-1,4,7,10-tetraazacyclododecane-1,4,7-triacetic Acid and One Molar Equivalent of Sodium Bromide 32.0 g (50.4 mmol) of the Dy complex of 10-(4-carboxy-1-methyl-2-oxo-3-azabutyl)-1,4,7,10-tetraazacyclododecane-1,4,7-triacetic acid described in Example 2 is dissolved in 200 ml of water and mixed with 5.19 g (50.4 mmol) of sodium bromide. The clear solution is then freeze-dried and finally further dried in a vacuum overnight at 100° C. A colorless powder is obtained.

Yield: 37.2 g (quantitative)
$H_2O$ content (Karl-Fischer): 3.5%
Dy determination (AAS): 20.8%
Elementary analysis (relative to anhydrous substance):
Cld: C 30.93 H 4.10 N 9.49 Dy 22.02 Na 3.12 Br 10.83 Fnd: C 30.81 H 4.29 N 9.31 Dy 21.70 Na 3.06 Br 10.42 b) Hexatriacontakis-amide Conjugate of the 36mer-polyamine of Example 13d with the Dysprosium Complex of 10-(4-carboxy-1-methyl-2-oxo-3-azabutyl)-1,4,7,10-tetraazacyclododecane-1,4,7-triacetic Acid 1.84 (0.2 mmol) of the 36mer-benzyloxycarbonylamine described in Example 13d is dissolved in glacial acetic acid and mixed with 33% hydrogen bromide in glacial acetic acid while being stirred. After 5 hours, the incipient precipitation is completed with diethyl ether, and the 36mer-amine-hydrobromide that is produced is washed with ether, dried in a vacuum and used in the reaction described below without additional purification.

Yield: 1.5 g (quantitative)

15.9 g (21.6 mmol, 3× excess) of the sodium bromide mixed salt, described in Example 31a above, with the dysprosium complex of 10-(4-carboxy-1-methyl-2-oxo-3-azabutyl)-1,4,7,10-tetraazacyclododecane-1,4,7-triacetic acid, 3.73 g (32.4 mmol) of N-hydroxysuccinimide, and 6.7 g (32.4 mmol) of N,N'-dicyclohexylcarbodiimide is dissolved in 100 ml of dimethyl sulfoxide at room temperature and preactivated for 60 minutes. A solution of 1.5 g (0.2 mmol) of the above-described hexatriaconta-hydrobromide and 3.5 g of triethylamine in 10 ml of water is added to the N-hydroxysuccinimide ester solution that is thus produced, and it is stirred overnight at room temperature. The suspension that is obtained is then mixed with sufficient acetone until complete precipitation occurs, the precipitate is suctioned off, dried, taken up in water, insoluble dicyclohexylurea is filtered out, and the filtrate is desalinated with an AMICON® YM-3 ultrafiltration membrane (cut off 3,000 Da), and low-molecular components are removed. The retentate is then freeze-dried.

Yield: 5.0 g (84% of theory)
H$_2$O content (Karl-Fischer): 10.5%
Dy determination (AAS): 19.6%
MALDI-TOF mass spectrum: 26.616 (M+Na$^+$)
Elementary analysis (relative to anhydrous substance):
Cld: C 40.24 H 5.35 N 13.11 Dy 22.00 Fnd: C 40.02 H 5.55 N 13.36 Dy 21.40

EXAMPLE 32 a) Mixture that Consists of the Gadolinium Complex of 10-(13-carboxy-1-methyl-2-oxo-3-azatridecyl)-1,4,7,10-tetraazacyclododecane-1,4,7-triacetic Acid and 2 Molar Equivalents of Lithium Chloride 38.1 g (50.4 mmol) of the Gd complex of 10-(13-carboxy-1-methyl-2-oxo-3-azatridecyl)-1,4,7,10-tetraazacyclododecane-1,4,7-triacetic acid described in Example 8c is dissolved in 250 ml of water and mixed with 4.27 g (100.8 mmol) of lithium chloride. The clear solution is then freeze-dried and finally further dried in a vacuum overnight at 100° C. A colorless powder is obtained.

Yield: 42.4 g (quantititive)
H$_2$O content (Karl-Fischer): 3.5%
Gd determination (AAS): 18.0%
Elementary analysis (relative to anhydrous substance):
Cld: C 40.00 H 5.75 N 8.33 Gd 18.70 Li 1.65 Cl 8.43 Fnd: C 39.73 H 5.99 N 8.51 Gd 18.17 Li 1.58 Cl 8.66 b) Hexaamide Conjugate of 6,6',6'',6''',6'''',6'''''-hexaamino-6,6',6'',6''',6'''',6'''''-hexadeoxy-α-cyclodextrin with the Gadolinium Complex of 10-(13-carboxy-1-methyl-2-oxo-3-azatridecyl)-1,4,7,10-tetraazacyclododecane-1,4,7-triacetic Acid 4.2 g (5 mmol) of the lithium mixed salt, described in Example 32a above, with the gadolinium complex of 10-(5-carboxy-1-methyl-2-oxo-3-azatridecyl)-1,4,7,10-tetraazacyclododecane-1,4,7-triacetic acid, 1.15 g (10 mmol) of N-hydroxysuccinimide, and 1.24 g (6 mmol) of dicyclohexylcarbodiimide is dissolved in 30 ml of dimethyl sulfoxide and stirred for 8 hours at room temperature. The N-hydroxysuccinimide ester solution that is thus produced is added to a suspension of 315 mg (0.25 mmol) of 6,6',6'',6''',6'''',6'''''-hexaamino-6,6',6'',6''',6'''',6'''''-hexadeoxy-α-cyclodextrin [J. Boger, R. J. Corcoran and J.-M. Lehn, Helv. Chim. Acta 61, 2190–2218 (1978)] in dimethyl sulfoxide, and it is stirred overnight at this temperature. The suspension that is obtained is then mixed with sufficient acetone until complete precipitation occurs, the precipitate is suctioned off, dried, taken up in water, insoluble dicyclohexylurea is filtered out, and the filtrate is desalinated with an AMICON® YM-3 ultrafiltration membrane (cut off 3,000 Da), and low-molecular components are removed. The retentate is then freeze-dried. A colorless powder is obtained.

Yield: 1.35 g (90% of theory)
H$_2$O content (Karl-Fischer): 9.5%
Gd determination (AAS): 16.6%
Elementary analysis (relative to anhydrous substance):
Cld: C 45.42 H 6.39 N 9.35 Gd 17.49 Fnd: C 45.13 H 6.20 N 9.57 Gd 17.11

EXAMPLE 33

Amide Conjugate of 3'-amino-3'-deoxyguanosine with the Gadolinium Complex of 1-[1-methyl-2-oxo-3-aza-4-carboxybutyl]-4,7,10-tris(carboxymethyl)-1,4,7,10-tetraazacyclododecane 1.163 g (1.588 mmol) of the title compound of Example 26a and 365.8 mg (3.176 mmol) of N-hydroxysuccinimide are dissolved in 10 ml of dimethyl sulfoxide and then cooled to 10° C. 393 mg (1.906 mmol) of dicyclohexylcarbodiimide is added at 10° C., and it is stirred for 45 minutes at room temperature. 422.8 mg (1.588 mmol) of 3'-amino-3'-deoxyguanosine, dissolved in 5 ml of dimethyl sulfoxide, and then 321.4 mg (3.176 mmol) of triethylamine are added to the N-hydroxysuccinimide ester solution that is thus produced. It is stirred overnight at room temperature. 200 ml of acetone is added in drops to this solution, the precipitate is filtered off, and it is rewashed twice with some acetone. The residue is purified by column chromatography (RP18/mobile solvent: gradient consisting of water/acetonitrile/tetrahydrofuran).

Yield: 1.36 g (90% of theory) of a colorless, flocculent powder after freeze-drying Water content: 7.4%
Elementary analysis (relative to anhydrous substance):
Cld: C 39.67 H 4.82 N 17.55 Gd 17.91 Fnd: C 39.48 H 4.94 N 17.38 Gd 17.76

EXAMPLE 34

Amide Conjugate of Dehydroabiethylamine with the Gadolinium Complex of 1-[1-methyl-2-oxo-3-aza-4-carboxybutyl]-4,7,10-tris(carboxymethyl)-1,4,7,10-tetraazacyclododecane 1.163 g (1.588 mmol) of the title compound of Example 26a and 365.8 mg (3.176 mmol) of N-hydroxysuccinimide are dissolved in 10 ml of dimethyl sulfoxide and then cooled to 10° C. 393 mg (1.906 mmol) of dicyclohexylcarbodiimide is added at 10° C., and it is stirred for 45 minutes at room temperature. 422.8 mg (1.588 mmol) of dehydroabiethylamine, dissolved in 5 ml of dimethyl sulfoxide, and then 321.4 mg (3.176 mmol) of triethylamine are added to the solution that is thus produced. It is stirred overnight at room temperature. 200 ml of acetone is added in drops to this solution, the precipitate is filtered off, and it is rewashed twice with some acetone. The residue is purified by column chromatography (RP18/mobile solvent: gradient consisting of water/acetonitrile/tetrahydrofuran).

Yield: 1.40 g (92% of theory) of a vitreous solid after freeze-drying

Water content: 6.5%

Elementary analysis (relative to anhydrous substance):
Cld: C 52.21 H 6.63 N 9.37 Gd 17.53 Fnd: C 52.35 H 6.81 N 9.20 Gd 17.38

EXAMPLE 35

Amide Conjugate of Ampicillin with the Gadolinium Complex of 1-[1-methyl-2-oxo-3-aza-4-carboxybutyl]-4,7,10-tris(carboxymethyl)-1,4,7,10-tetraazacyclododecane 1.135 g (1.588 mmol) of the title compound of Example 25a and 365.8 mg (3.176 mmol) of N-hydroxysuccinimide are dissolved in 10 ml of dimethyl sulfoxide and then cooled to 10° C. 393 mg (1.906 mmol) of dicyclohexylcarbodiimide is added at 10° C., and it is stirred for 45 minutes at room temperature. 554.9 mg (1.588 mmol) of ampicillin, dissolved in 5 ml of dimethyl sulfoxide, and then 482 mg (4.764 mmol) of triethylamine are added to the solution that is thus produced. It is stirred overnight at room temperature. 200 ml of acetone is added in drops to this solution, the precipitate is filtered off, and it is rewashed twice with some acetone. The residue is purified by column chromatography (RP18/mobile solvent: gradient consisting of water/acetonitrile/tetrahydrofuran/+0.5% trifluoroacetic acid).

Yield: 1.54 g (90% of theory) of a colorless, flocculent powder after freeze-drying Water content: 10.0%

Elementary analysis (relative to anhydrous substance):
Cld: C 45.76 H 4.88 N 10.10 S 3.30 Gd 16.19 Fnd: C 45.61 H 5.10 N 10.00 S 3.20 Gd 16.05

EXAMPLE 36

Amide Conjugate of Pentapeptide $NH_2$-Val-Leu-Phe-Phe-Ala-OH with the Gadolinium Complex of 1-[1-methyl-2-oxo-3-aza-4-carboxybutyl]-4,7,10-tris(carboxymethyl)-1,4,7,10-tetraazacyclododecane 1.135 g (1.588 mmol) of the title compound of Example 25a and 365.8 mg (3.176 mmol) of N-hydroxysuccinimide are dissolved in 10 ml of dimethyl sulfoxide and then cooled to 10° C. 393 mg (1.906 mmol) of dicyclohexylcarbodiimide is added at 10° C., and it is stirred for 45 minutes at room temperature. 946 mg (1.588 mmol) of the pentapeptide $NH_2$-Val-Leu-Phe-Phe-Ala-OH (produced according to the solid-phase technique), dissolved in 5 ml of dimethyl sulfoxide, and then 321.4 mg (3.176 mmol) of triethylamine are added to the suspension that is thus produced. It is stirred overnight at room temperature. 200 ml of acetone is added in drops to this suspension, the precipitate is filtered off, and it is rewashed twice with some acetone. The residue is purified by column chromatography (RP18/mobile solvent: gradient consisting of water/acetonitrile/tetrahydrofuran).

Yield: 1.81 g (87% of theory) of a colorless, flocculent powder after freeze-drying Water content: 8.1%

Elementary analysis (relative to anhydrous substance):
Cld: C 50.73 H 6.09 N 11.60 Gd 13.02 Fnd: C 50.54 H 6.19 N 11.41 Gd 12.80

EXAMPLE 37

Amide Conjugate of N-methylglucosamine with the Gadolinium Complex of 1-[1-methyl-2-oxo-3-aza-4-carboxybutyl]-4,7,10-tris(carboxymethyl)-1,4,7,10-tetraazacyclododecane 1.163 g (1.588 mmol) of the title compound of Example 26a is dissolved in 10 ml of dimethyl sulfoxide and then cooled to 10° C. 310 mg (1.588 mmol) of D(-)-N-methylglucosamine and 785.4 mg (3.176 mmol) of 2-ethoxy-1-ethoxycarbonyl-1,2-dihydroquinoline (EEDQ) are added at 10° C. It is stirred overnight at room temperature. 200 ml of acetone is added in drops to this solution, the precipitate is filtered off, and it is rewashed twice with some acetone. The residue is purified by column chromatography (RP18/mobile solvent: gradient consisting of water/acetonitrile/tetrahydrofuran).

Yield: 1.30 g (93% of theory) of a colorless, flocculent powder after freeze-drying Water content: 8.5%

Elementary analysis (relative to anhydrous substance):
Cld: C 38.70 H 5.62 N 10.41 Gd 19.49 Fnd: C 38.55 H 5.80 N 10.30 Gd 19.29

We claim:

1. A process for the production of a metal-complex carboxylic acid amide, which comprises pretreating a metal-complex carboxylic acid mixture, comprising a metal-complex carboxylic acid having at least one noncomplexed carboxyl group and at least one solubilizing substance in dimethyl sulfoxide, with a dehydrating reagent, optionally with the addition of a coupling adjuvant, and then reacting the resulting mixture with an amine of formula I

$$A(NH_2)_n \quad (I),$$

in which

A stands for the radical of a natural or synthetic amine, and n stands for numbers 1 to 100 to form amide(s) between the said non-complexed carboxyl group and the amine group(s).

2. Process according to claim 1, wherein the metal-complex carboxylic acid mixture is formed in situ by the addition of solubilizing substance(s) to the DMSO suspension of metal-complex carboxylic acid, dehydrating reagent and optionally a coupling adjuvant.

3. Process according to claim 1, wherein first the metal-complex carboxylic acid mixture is produced and isolated, and then the latter is pretreated in DMSO with the addition of a dehydrating reagent and optionally a coupling adjuvant.

4. Process according to claim 1, wherein the amine is added without a solvent to the DMSO solution of the pretreated metal-complex carboxylic acid mixture.

5. Process according to claim 1, wherein the amine is added in dissolved form to the DMSO solution of the pretreated metal-complex carboxylic acid mixture.

6. Process according to claim 5, wherein the amine is dissolved in DMSO, water or in solvents that are mixed with water.

7. Process according to claim 1, wherein the pretreatment is carried out with the dehydrating reagent at temperatures of 0 to 50° C. and at reaction times of between 1 and 24 hours.

8. Process according to claim 7, wherein the pretreatment is carried out at room temperature and at reaction times of between 3 and 12 hours.

9. Process according to claim 1, wherein the reaction is carried out with the amine of general formula I at temperatures of 0 to 70° C. and at reaction times of between 1 and 48 hours.

10. Process according to claim 9, wherein the reaction is carried out at temperatures of 30 to 60° C. and at reaction times of between 8 and 24 hours.

11. Process according to claim 1, wherein the solubilizing substances are selected from alkali, alkaline-earth, trialkylammonium and tetraalkylammonium salts; ureas, N-hydroxyimides, hydroxyaryltriazoles, substituted phenol, and salts of heterocyclic amines.

12. Process according to claim 1, wherein n stands for the number 1.

13. Process according to claim 1, wherein n stands for the numbers 2 to 50.

14. Process according to claim 1, wherein n stands for the numbers 12 to 36.

15. Process according to claim 1, wherein the metal-complex carboxylic acid has a cyclic structure.

16. Process according to claim 11, wherein the solubilizing substances are selected from the compounds lithium chloride, lithium bromide, lithium iodide, sodium bromide and sodium iodide.

17. Process according to claim 1, wherein the amines of general formula I $A(NH_2)_n$ stand for dendrimers, proteins, polylysine, aminopolysaccharides, polyvinylamines, polyalkylamines, poly[N-(2-aminoethyl)]methacrylamides, polynucleotides, polypeptides, antibiotics, nucleosides, aminoterpenes, aminoporphyrins, aminosteroids and amino sugars.

18. Process according to claim 15, wherein the metal-complex carboxylic acid stands for a lanthanide, iron, manganese, yttrium and bismuth complex of compounds with the 1,4,7,10-tetraazacyclododecane skeleton.

19. Process according to claim 18, wherein the metal-complex carboxylic acid stands for a gadolinium or dysprosium complex.

20. Process according to claim 18, wherein the metal-complex carboxylic acid stands for a compound of general formula II

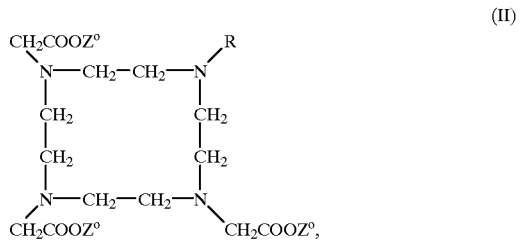

(II)

whereby $Z^0$ stands for a metal ion equivalent of atomic numbers 25, 26, 39, 57–71, 83 and R stands for a $CHX^1$—CO—NH—$CHY^1$—$(CH_2)_f$—COOH group, in which $X^1$ and $Y^1$, independently of one another, mean a hydrogen atom, a straight-chain or branched $C_1$–$C_7$ alkyl radical, a phenyl or benzyl group, and f means numbers 0 to 9.

21. Process according to claim 20, wherein the metal-complex carboxylic acid of general formula II stands for a gadolinium or dysprosium complex of 10-[4-carboxy-1-methyl-2-oxo-3-azabutyl]-1,4,7,10-tetraazacyclododecane-1,4,7-triacetic acid.

22. Process according to claim 17, wherein radical A of the amine of general formula I does not contain any amino groups that can be protonated.

23. Process according to claim 22, wherein the amine of general formula I stands for a 24mer polyamine based on N,N,N',N',N'',N''-hexakis[2-(trilysyl-amino)-ethyl]-trimesic acid triamide.

24. Process according to claim 1, wherein the metal-complex carboxylic acid mixture contains up to 5 molar equivalents of the solubilizing substance relative to the metal-complex carboxylic acid.

25. Process according to claim 1, wherein the metal-complex carboxylic acid mixture contains 0.5 to 2 molar equivalents of the solubilizing substance relative to the metal-complex carboxylic acid.

26. Process according to claim 1, wherein carbodiimide or onium reagents are used as a dehydrating reagent.

27. Process according to claim 26, wherein dicyclohexylcarbodiimide is used as a carbodiimide.

28. Process according to claim 1, wherein 4-nitrophenol, N-hydroxysuccinimide, 1-hydroxybenzotriazole, 1-hydroxy-7-azabenzotriazole, 3,5-dinitrophenol or pentafluorophenol is used as a coupling adjuvant.

29. Process according to claim 28, wherein 4-nitrophenol is used as a coupling adjuvant.

30. Process according to claim 1, wherein first a mixture of the gadolinium complex of 10-[4-carboxy-1-methyl-2-oxo-3-azabutyl)-1,4,7,10-tetraazacyclododecane-1,4,7-triacetic acid and 1 to 2 equivalent(s) of sodium bromide is produced and isolated, and the latter is then pretreated with the addition of 4-nitrophenol and dicyclohexylcarbodiimide in DMSO at room temperature and at reaction times of between 3 and 12 hours, and then optionally it is reacted with the addition of water with the 24mer polyamine based on N,N,N',N',N'',N''-hexakis[2-(trilysylamino)-ethyl]-trimesic acid triamide at 20 to 60° C. and at reaction times of between 8 and 24 hours.

31. Process according to claim 1, wherein first a mixture of the gadolinium complex of 10-[4-carboxy-1-methyl-2-oxo-3-azabutyl)-1,4,7,10-tetraazacyclododecane-1,4,7-triacetic acid and 1 to 2 equivalent(s) of lithium chloride is produced and isolated, and the latter then is pretreated with the addition of 4-nitrophenol and dicyclohexylcarbodiimide in DMSO at room temperature and at reaction times of between 3 and 12 hours, and then optionally it is reacted with the addition of water with the 24mer polyamine based on N,N,N',N',N'',N''-hexakis[2-(trilysylamino)-ethyl]-trimesic acid triamide at 20 to 60° C. and at reaction times of between 8 and 24 hours.

* * * * *